(12) United States Patent
Galbierz et al.

(10) Patent No.: US 10,849,704 B2
(45) Date of Patent: Dec. 1, 2020

(54) MEDICAL DRAPE

(71) Applicants: Thomas R. Galbierz, Brentwood, TN (US); Michael A. Galbierz, St. Louis, MO (US)

(72) Inventors: Thomas R. Galbierz, Brentwood, TN (US); Michael A. Galbierz, St. Louis, MO (US)

( * ) Notice: Subject to any disclaimer, the term of this patent is extended or adjusted under 35 U.S.C. 154(b) by 56 days.

(21) Appl. No.: 16/072,755

(22) PCT Filed: Feb. 16, 2017

(86) PCT No.: PCT/US2017/018171
§ 371 (c)(1),
(2) Date: Jul. 25, 2018

(87) PCT Pub. No.: WO2017/143066
PCT Pub. Date: Aug. 24, 2017

(65) Prior Publication Data
US 2019/0336233 A1 Nov. 7, 2019

Related U.S. Application Data

(60) Provisional application No. 62/296,988, filed on Feb. 18, 2016.

(51) Int. Cl.
*A61B 46/20* (2016.01)
*A61F 13/02* (2006.01)
(Continued)

(52) U.S. Cl.
CPC .......... *A61B 46/20* (2016.02); *A61F 13/0259* (2013.01); *A61M 39/02* (2013.01);
(Continued)

(58) Field of Classification Search
CPC ......... A61B 46/20; A61B 46/00; A61B 46/27; A61B 46/40; A61B 46/30; A61B 90/80;
(Continued)

(56) References Cited

U.S. PATENT DOCUMENTS 4,485,809 A * 12/1984 Dellas ..................... A61L 15/26
602/52
4,642,107 A * 2/1987 Arnone ................... A61F 5/448
604/342

(Continued)

FOREIGN PATENT DOCUMENTS

JP 2011004850 A 1/2011
WO PCT/US2014/013563 * 7/2014 ............. A61B 17/02

OTHER PUBLICATIONS

International Search Report for corresponding PCT/US2017/018171, dated May 10, 2017.
(Continued)

*Primary Examiner* — Kari K Rodirquez
(74) *Attorney, Agent, or Firm* — Sandberg Phoenix & von Gontard, P.C.

(57) ABSTRACT

A medical drape comprises at least a bottom ply in the form of a release liner, a middle ply which is adhered to the patient during use of the drape, and a top ply covering the middle ply. The middle ply having an adhesive applied to a bottom surface thereof to removably adhere the bottom ply to the middle ply. The drape comprises a drape body defining top and bottom edges and first and second side edges; a first liner release tab and a carrier lift tab, both tabs being at an edge of the body. The first liner release tab is operable to remove the bottom ply from the middle ply to expose the adhesive of the middle ply. The carrier lift tab is operable to remove the top ply from the middle ply after application of the middle ply to a patient.

25 Claims, 13 Drawing Sheets

(51) Int. Cl.
  *A61M 39/02* (2006.01)
  *B32B 3/26* (2006.01)
  *B32B 5/02* (2006.01)
  *B32B 27/32* (2006.01)
  *B32B 27/36* (2006.01)
  *B32B 27/40* (2006.01)

(52) U.S. Cl.
  CPC ......... *A61B 2046/205* (2016.02); *B32B 3/266* (2013.01); *B32B 5/028* (2013.01); *B32B 27/32* (2013.01); *B32B 27/36* (2013.01); *B32B 27/40* (2013.01); *B32B 2250/03* (2013.01); *B32B 2255/02* (2013.01); *B32B 2255/12* (2013.01); *B32B 2255/26* (2013.01); *B32B 2307/50* (2013.01); *B32B 2307/724* (2013.01); *B32B 2307/732* (2013.01); *B32B 2405/00* (2013.01)

(58) Field of Classification Search
  CPC .............. A61B 90/00; A61B 2046/201; A61B 2046/205; A61B 2046/236; A61B 46/23; A61B 2046/234; A61F 13/00; A61F 13/00089; A61F 13/02; A61F 13/0259; A61F 2013/00604; A61F 2013/00627; A61F 2013/00655; A61F 13/024; A61F 13/0266; A61F 2013/00812; A61F 2013/00817; A61F 2013/008; A61F 2013/00804; A61F 15/005; A61F 13/00085; A61F 13/008; A61M 1/008; A61M 1/009; A61M 2025/0266; A61M 2025/0273; A61M 25/02; B32B 7/06; B32B 2037/262
  USPC ........................................................ 128/849
  See application file for complete search history.

(56) References Cited

U.S. PATENT DOCUMENTS

| | | | | |
|---|---|---|---|---|
| 4,664,106 | A | * | 5/1987 | Snedeker .............. A61F 13/023 602/52 |
| 5,266,371 | A | * | 11/1993 | Sugii .................... A61F 13/023 428/131 |
| 5,538,012 | A | | 7/1996 | Wieder et al. |
| 5,599,289 | A | | 2/1997 | Castellana |
| 5,704,905 | A | * | 1/1998 | Jensen ................ A61F 13/0259 602/42 |
| 5,755,681 | A | * | 5/1998 | Plews ................... A61F 13/023 602/52 |
| 5,979,450 | A | | 11/1999 | Baker et al. |
| 5,985,395 | A | | 11/1999 | Comstock et al. |
| 5,998,694 | A | * | 12/1999 | Jensen ................. A61F 13/023 602/43 |
| 8,277,916 | B2 | | 10/2012 | Cockman et al. |
| 2003/0014031 | A1 | * | 1/2003 | Tanzer .............. A61F 13/53436 604/385.16 |
| 2006/0137262 | A1 | * | 6/2006 | Crowder-Moore ....... E06B 1/62 52/58 |
| 2012/0199268 | A1 | * | 8/2012 | Popp ................. A61F 13/15723 156/73.1 |
| 2012/0255562 | A1 | | 10/2012 | McGuire, Jr. |
| 2012/0312308 | A1 | * | 12/2012 | Allen ..................... A61B 46/00 128/853 |
| 2013/0152944 | A1 | * | 6/2013 | Okada .................... A45D 44/12 128/846 |
| 2014/0031735 | A1 | * | 1/2014 | Zurovcik ............. A61M 1/0011 602/54 |
| 2015/0005688 | A1 | * | 1/2015 | Goby .................. A61F 13/0253 602/54 |
| 2015/0335322 | A1 | | 11/2015 | Galbierz et al. |

OTHER PUBLICATIONS

Written Opinion for corresponding PCT/US2017/018171, dated May 10, 2017.

* cited by examiner

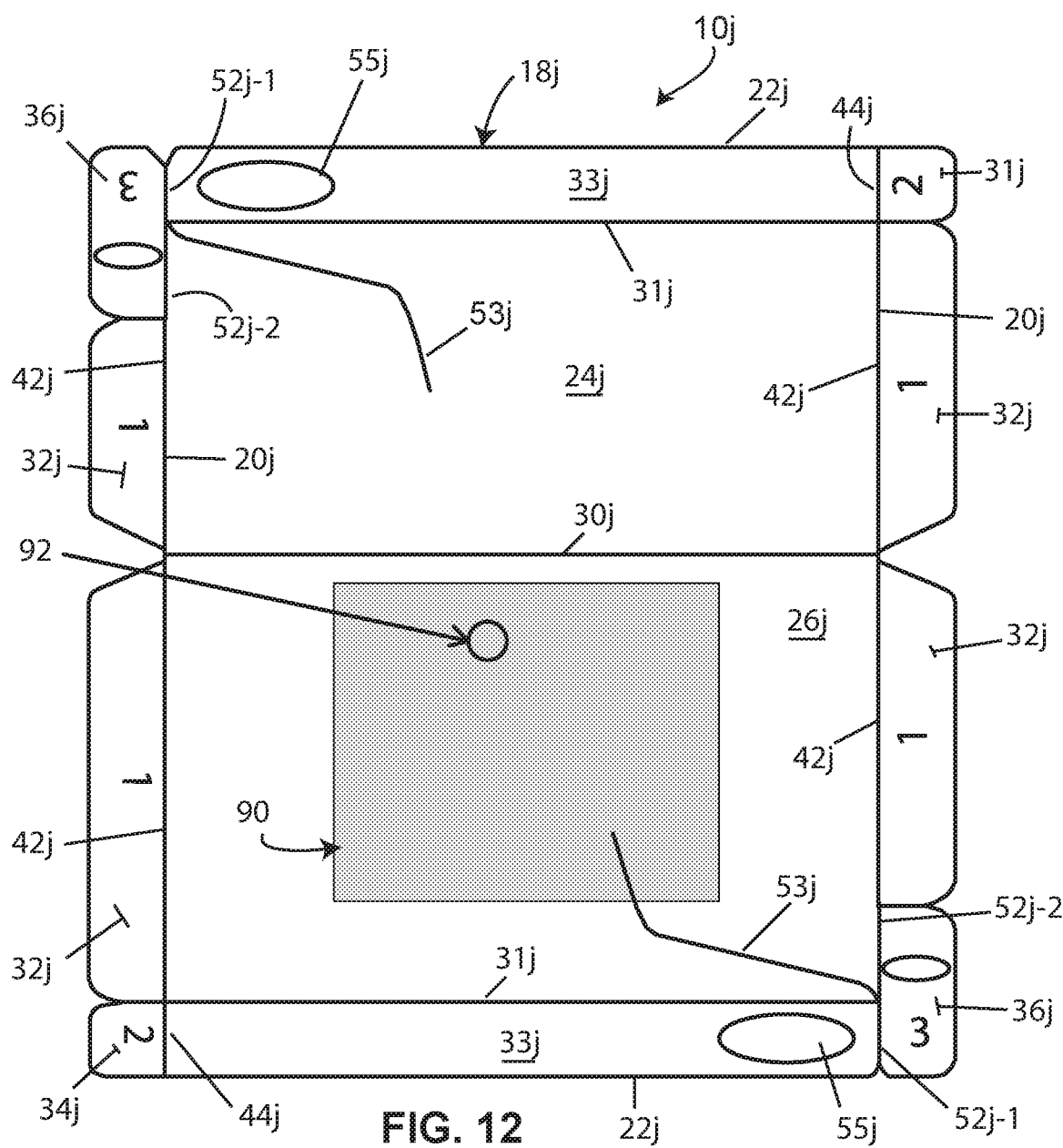
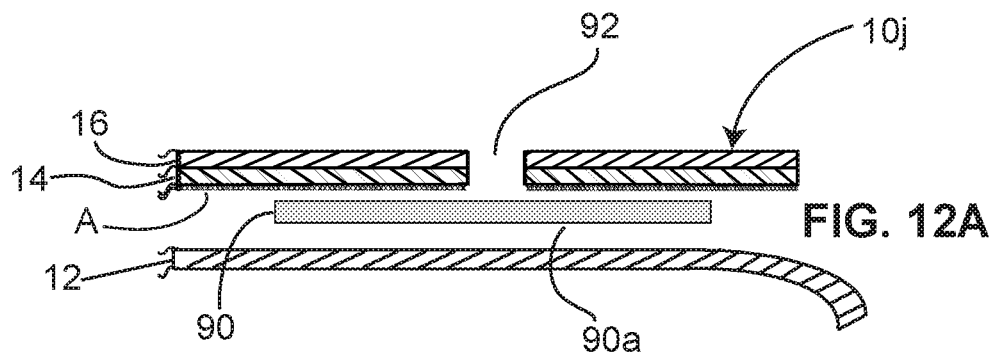
FIG. 12
FIG. 12A

MEDICAL DRAPE

CROSS-REFERENCE TO RELATED APPLICATIONS

This application is the US National Stage under 35 USC § 371 of International App. No. PCT/US2017/018171 filed Feb. 16, 2017 which claims priority to U.S. patent application Ser. No. 62/296,988 filed Feb. 18, 2016, entitled "Medical Drape," all of which are incorporated herein by reference.

STATEMENT REGARDING FEDERALLY SPONSORED RESEARCH OR DEVELOPMENT

Not Applicable.

BACKGROUND OF THE INVENTION

The present invention relates to medical/surgical drape, and in particular, to an incisable film that can be adhered to a patient at a surgical site on the patient (i.e., the patient's abdomen, thorax, back, thigh, etc.) to help maintain a sterile field around the medical/surgical site on the patient.

Surgical or medical drapes and incisable films are used to maintain a surgical/procedural area on the patient clean and sterile during surgical/medical procedures. Drapes have been made which are adhered to the patient. However, such drapes could be improved to increase the ease of handling the drape and to increase the functionality of the drape.

SUMMARY

Briefly stated, a medical drape is formed from a multi-ply film comprised of at least a bottom ply in the form of a release liner, a middle ply which is adhered to the patient during use of the drape, and a top (or carrier) ply. The middle ply has an adhesive applied to its bottom surface to removably adhere the bottom ply to the middle ply.

The drape comprises a drape body defining top and bottom edges and first and second side edges, a first liner release tab and a carrier (or top ply) lift tab. The first liner release tab has an inner edge defined by a top-middle cut, such that operation of the first liner release tab will pull the bottom ply from the middle ply to expose the adhesive of the middle ply; and the carrier lift tab has an inner edge defined by a bottom-middle cut, such that operation of the carrier lift tab removes the top ply from the middle ply.

The medical drape can further comprise a press down area adjacent the carrier lift tab. A user can press against the press down area when the carrier lift tab is being pulled to prevent the middle ply from being pulled off the patient as the top ply is removed from the middle ply. In one embodiment, the press down area can be defined by a top cut extending inwardly into the body; the top cut being substantially co-linear with an edge of the carrier lift tab. In this variation, the medical drape can include a separation handle extending from the body adjacent the liner release tab. The separation handle is separated from the drape body by a bottom cut. Additionally, in this embodiment, the cuts separating the tabs from the drape body are formed such that upon application of the drape to a patent, and upon removal of the top ply from the middle ply, none of the tabs remain with the drape body.

In another embodiment of the press down area, the press down area is defined by a tab extending from the body. In this instance, the press down tab has an inner edge defined by a top cut.

In a variation of the press down tab, the top cut defining the inner edge of the press down tab extends the full length of the press down tab.

In another variation of the press down tab, the top cut defining the inner edge of the press down tab extends from an edge of the press down tab adjacent the carrier lift tab only a portion of the length of the press down tab, such that the top ply of the press down tab is connected to the top ply of the body, such that the top ply of the press down tab will be removed when the carrier lift tab is pulled to remove the top ply from the middle ply.

In a variation of the drape, the medical drape includes at least one bottom cut in the bottom ply extending from one side edge to the other of the drape body to divide the drape into a first section and a second section. One of the first and second sections is a positioning section, and the first liner release tab is associated with this first section. The carrier release and press down tabs are associated with one of the first and second sections, and the drape additionally includes a second liner release tab associated with the second section.

In a variation of the drape, the drape can further include a second liner release tab at an edge of the body opposite the first liner release tab.

In accordance with an aspect of the drape, the middle ply has a stretchability factor greater than a stretchability factor of the top ply. The stretchability factor of the middle ply can be at least 200%.

In accordance with another aspect of the drape, the medical drape can be provided with a liftable panel defined by a top cut extending from one side of the drape body to the opposite side of the drape body, a perforated top cut extending across the body spaced from the top cut, and a carrier lift tab associated with the top ply liftable panel; whereby, the top ply liftable panel can be raised from the middle ply to allow for stretching of the middle ply prior to application of the middle ply to a surface.

In accordance with another aspect of the invention, the medical drape can be provided with an access port assembly comprised of a flange which is adhered to the adhesive of the middle ply and a hollow neck which extends through an access port aperture in the middle and top plies of the drape body. The access port aperture is pre-formed in the drape body. In a variation of the access port, the access port is defined by an outer bottom cut and an inner top-middle cut surrounded by the outer bottom cut. The outer bottom cut defines a hole in the bottom ply sized to receive the flange of the port assembly, and the inner top-middle ply defines a hole extending through the top and middle plies sized to allow passage of the access port neck therethrough. In this instance, the access port aperture is formed by removing the material inside of the outer bottom cut and inner top-middle cut from the drape. In another variation, the access port aperture is defined by concentric holes in the top and middle ply, and the access port assembly is secured to the drape, as supplied.

In another aspect of the drape, the drape of can be provided with a grasping panel extending across the body at an end of the body. In this instance, the grasping panel is separated from the remainder of the body by a bottom middle cut such that the bottom ply of the grasping panel remains with the grasping panel when the bottom ply is removed from the remainder of the body. In this variation, the drape is also preferably provided with a release liner tab associated with the grasping panel operable to remove the bottom ply of the grasping panel to expose the adhesive of the middle ply of the grasping panel. To this end, the tab associated with the grasping panel is separated from the main portion of the grasping panel by a top-middle cut.

In the drape with the grasping panel, the carrier lift tab can extend from an end of the drape adjacent the grasping panel to a point beyond an inner edge of the grasping panel. In this instance, the carrier lift tab is separated from the grasping panel by a full cut; and a remainder of the carrier lift tab is separated from the drape body by a bottom-middle cut. To further facilitate removal of the top ply, this drape can also include a top cut extending diagonally inwardly from a corner of said grasping panel adjacent said carrier lift tab. In a variation, the top-cut can extend diagonally across the drape, such that the top ply is removed from the drape in two sections.

In another variation, the drape can be provided with a sheet which is pre-adhered to, or adherable to, the adhesive of the middle ply. This sheet has a non-adhesive surface, such that the drape will present an adhesive-free area which can be applied against a wound. This sheet is made, at least in part, from a material which will prevent ingrowth of the wound to the material as the wound heals.

In one variation, the sheet can be made from a material which will permit moisture, vapor, and gas to pass therethrough. In this instance, the drape can include an aperture formed, or formable, in said drape material above the sheet. The drape can then be adapted to connect the aperture to a vacuum source, such that said drape can be used for negative pressure wound therapy.

In a further variation, the sheet can be comprised of two or more plies. The plies selected from material which can act as a filter, can be adapted to provide medicament to the wound, contain sensors for monitoring biometric and/or physiological parameters (such as temperature, gas concentrations, presence of pathogens, etc.), and or which operate as a check valve. In this variation, the material that will be adjacent the wound presents an adhesive-free surface to the wound.

BRIEF DESCRIPTION OF THE SEVERAL VIEWS OF THE DRAWINGS

FIG. 12 is a plan view of a further variation of the drape, and wherein the drape is provided with an optional non-adhesive material which can be positioned over a wound;

FIG. 12A is a cross-sectional view of the drape of FIG. 12;

Corresponding reference numerals will be used throughout the several figures of the drawings.

DETAILED DESCRIPTION OF THE INVENTION

Figure 1:
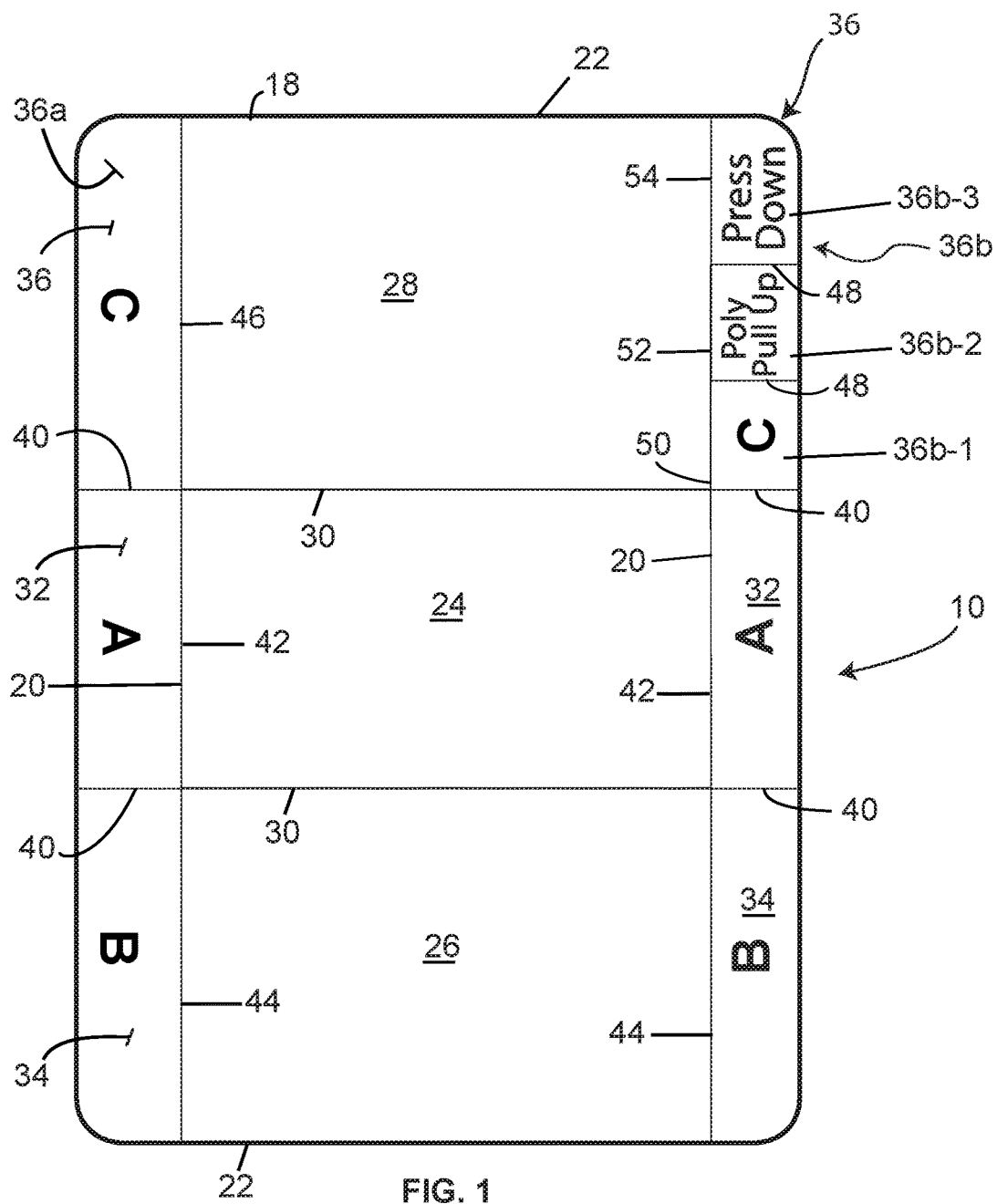
FIG. 1 is a plan view of a medical/surgical drape.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Figure 1A:
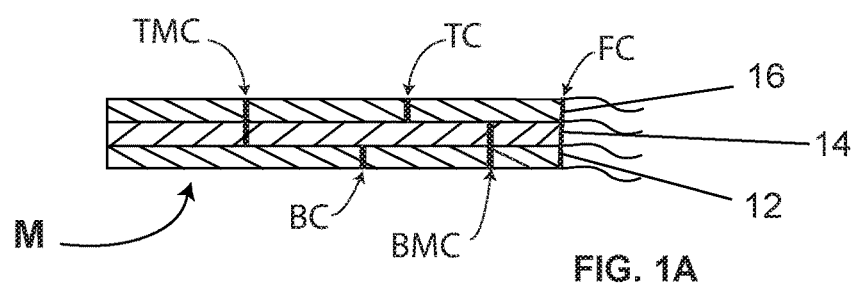
FIG. 1A is a schematic cross-sectional view of the drape demonstrating various cuts/slices through the film from which the drape is formed.

Referring initially to FIGS. 1 and 1A, a drape 10 is illustratively shown in both plan and cross-section. The drape 10 is made (such as by die-cutting) from a multi-ply material M. The material M can be a 3-ply material comprised of a bottom ply 12, a middle ply 14, and a top ply 16. The bottom ply 12 is preferably a release liner, and can be made, for example, of a substantially non-stretchable material, such as Kraft paper. The middle ply 14 is preferably a polymer film having a substantial amount of stretch in at least one direction; and the top ply 16 (sometimes referred to as a carrier ply) is made from a polymer film different from the middle ply and which has, at best, only slight stretchability. The middle ply has a lower surface coated with a hypoallergenic pressure sensitive adhesive (such as an acrylic or silicone adhesive) to removably secure the bottom ply release liner 12 to the middle ply 14. The top ply 16 is adhered to the middle ply 14 without the use of an adhesive. For example, the top ply 16 can be adhered to the middle ply 14 or it can self-adhere to the middle ply 14 by means of co-adhesion.

One preferred material for the drape 10 is 3M 9836 medical tape or film (available from 3M). In this tape, the bottom ply 12 is comprised of a non-stretchable silicone coated paper, which is, for example, about 5 mil (about 0.127 mm) thick. The middle ply 14 is a polyethylene film having an acrylic adhesive applied to a bottom side thereof, to removably secure the bottom, paper, ply to the middle ply. The middle ply is highly conformable and stretchable, having a high percentage or degree of elongation/stretchability, i.e., 200%-500%. Additionally, this middle ply is typically breathable. The middle ply can have a thickness of about 1 mil (about 0.03 mm). The top ply can be a polyolefin film with a thickness of about 2.5 mil (about 0.06 mm). The top ply can be slightly stretchable. For example, the top ply can have an elongation of less than about 10%. As such, the top ply is substantially non-stretchable. The top ply is liquid impermeable, and preferably also air impermeable. The overall tape (paper liner, middle ply, and top ply) has a thickness of about 7.5 mil (about 0.2 mm). When the bottom ply 12 is still adhered to the middle ply 14, the tape, as a whole, is substantially not stretchable. Another preferred material from which the drape can be made is a silicone gel adhesive tape available from Polymer Science, Inc. under the name P-DERM® PS-1829. This tape comprises a high adhesion silicone gel skin contact adhesive which is coated on the bottom of the middle ply. The silicone adhesive has an adhesion of 2.8N/25 mm as determined by a QSP-723 testing method. The tape has a polyurethane bottom ply release layer that is about 25 microns thick, a polyester middle ply that is about 50 microns thick and a 63# kraft paper top ply. The overall thickness of the tape is thus about 0.18 mm. However, the drape 10 can be formed from any desired sheet of material which is otherwise suitable for the use to which the drape will be put.

The drape 10, as noted, can be formed by die-cutting, and thus the drape, in an as-supplied form, includes (1) top cuts TC which extend only through the top ply 16; (2) top/middle cuts TMC which extend through the top and middle plies 16 and 14, but which do not extend through the bottom ply 12; (3) full cuts FC which extend through all the plies of the as-supplied drape; (4) bottom cuts BC which extend only through the bottom ply 12; and (5) bottom/middle cuts BMC which extend through the bottom and middle plies 12 and 14, but do not extend through the top ply 16. See FIG. 1 A. In addition, and for purposes set forth below, the cuts or slices can be formed as perforated cuts, rather than continuous cuts. Unless otherwise noted, the cuts are continuous cuts (rather than perforated cuts). The purpose for the different cuts will become explained more fully below.

The drape 10 (FIG. 1) comprises a body 18 having elongated side edges 20 and top and bottom edges 22. The body 18 is divided into three sections (a middle section 24, a first end section 26, and a second end section 28) by bottom cuts 30 which extend generally perpendicularly between the side edges 20 of the body 18. The drape 10 is shown divided into approximately equal thirds, however, the sizes of the three sections could be altered, if desired. Further, the drape 10 could be made with only two sections or four or more sections, if desired.

Tabs 32, 34, and 36 extend from both side edges 20 of the drape body 18. As seen, the tabs, in combination, extend the full length of the body sides 20. The tabs are separated from each other by full cuts 40 which are co-linear with the bottom cuts 30, and extend the width of the tabs. The tabs are separated from the body 18 by cuts (as described below) which extend at least through the top ply of the tape. As shown, tabs extend from both sides of the drape body 18. However, as described below, the drape could be provided with tabs extending from only one side of the body.

The tabs 32 and 34 (labeled as A-Tabs and B-Tabs) are associated with the middle section 24 and first end section 26, respectively, of the drape body 18. The tabs 32 and 34 are separated from body 18 by top-middle cuts 42 and 44, respectively. Thus, the bottom ply is uninterrupted across the width of the drape in middle and first end sections of the body. Therefore, when one of the A-tabs 32 or B-tabs 34 are pulled downwardly away from the drape body 18, the top and middle plies of the tabs will remain with the bottom ply of the tab, and the bottom ply (or release liner) will be removed from the respective (middle or first end) section of the drape to expose the adhesive on the underside of the respective section of the middle ply.

The tabs 36 on the opposite sides of the body are associated with the second end section 28 of the body and are different from each other. One tab 36a (labeled as the C-Tab on the left side of FIG. 1), is essentially identical to the tabs 32 and 34, and is separated from the drape body 18 by a top-middle cut 46. The tab 36a is thus operable to remove the release liner or bottom ply of the film from the middle ply to expose the adhesive of the middle ply in the end section 28. The opposite tab 36b, on the other hand, is subdivided into three tabs or sections 36b-1, 36b-2, and 36b-3. The tabs or sections 36b-1, 36b-2, and 36b-3 are separated from each other by full cuts 48 which extend the full width of the tabs or sections.

The tab 36b-1 is adjacent the A-tab 32, and is separated from the A-tab by the full cut 40. This first tab section 36b-1 is separated from the drape body by a top-middle cut 50, similarly to tabs 32, 34 and 36a. The top and middle plies of this first section 36b-1 are thus separated from the top and middle plies of the body, and the bottom ply of the tab section 36b-1 remains connected to the bottom ply of the body. This first end section tab 36b-1 is labeled, in the drawing, as a "C" tab, and is operable to remove the release liner or bottom ply of the film from the middle ply to expose the adhesive of the middle ply in the end section 28.

The second (middle) end section tab 36b-2 is separated from the body by a bottom-middle cut 52. Thus, the top ply of the tab 36b-2 remains connected with the top ply of the body, and the middle and bottom plies are separated from the middle and bottom plies in the body. This middle tab 36b-2 is labeled as a "Poly Pull Up" tab in the FIG. 1, and is operable to remove the top ply 16 from the middle ply 14 of the tape.

Lastly, the third end section of tab 36b-3 is separated from the body 18 by a top cut 54. Thus, the top ply of the tab 36b-3 is separated from the top ply of the body 18, and the middle and bottom plies of the tab remain connected to the middle and bottom plies of the body. As such, when the C-tab 36b-1 is pulled, the bottom ply (release liner) will be removed from the end section 36b-3 to expose the adhesive of the tab end section 36b-3. This third tab 36b-3 is labeled as a "Press Down" tab. Its function will be explained below.

In use, the drape is applied to a patient at a surgical/medical site on the patient after the surgical site (for example abdomen, back, thoracic area, etc.) after the patient is scrubbed and prepped. Initially, either one of the A-tabs 32 is pulled away from the drape body 18 to remove the bottom ply 12 (the release liner) from the middle section 24 of the drape body 18 to expose the adhesive of the middle ply in the middle section of the drape. The release liner will remain with the drape in the end sections 26 and 28 at this point in the application procedure, and therefore, the medical personnel can manipulate the drape without contacting the adhesive by holding the drape at the end sections. With the drape in this state, the drape can be applied to the patient. Because the middle section 24 is adhered to the patient first, it can be termed a "positioning" portion of the drape.

With the middle section 24 of the drape adhered to the patient, the medical personnel next grab one of the B-tabs 34, and pull the B-tab away from the body 18 while holding the drape body away from the patient. This will remove the bottom ply (release liner) from the first end section 26 of the body, to expose the adhesive of the middle ply of the body first end section. The body first end section can then be smoothed out over the patient's skin and adhered to the patent.

Lastly, the body second end section 28 is adhered to the patient. The second end section 28 is held away from the patient, and medical personnel hold either the C-tab 36*a* or the C-tab 36*b*-1 and pull the tab away from the drape body to expose the adhesive of the middle ply in the second end section 28. This will remove the bottom ply (release liner) from the second end section 28 of the body, to expose the adhesive of the middle ply of the body second end section. The tab 36*b*-2 is separated from the body 18 by a bottom-middle cut, and thus, the bottom ply (release liner) will remain with the tab 36*b*-2. The tab 36*b*-3, however, is separated from the body by a top cut, and thus the release liner (bottom ply) of the tab 36*b*-3 will be removed from the tab 36*b*-3 when the bottom ply (release liner) is removed from the body second end section 28. Once the release liner has been removed from the body second end section, the body second end section 28 can be smoothed out over the patient's skin and adhered to the patent.

As can be appreciated, the drape body 18, when applied to the patient, will comprise two plies—the middle ply 14 (which will be adhered to the patient's skin) and the top ply 16. Further, both tabs 34, both tabs 32, and the tab 36*a* will have been separated from the drape body 18. The tabs 36*b*-2 and 36*b*-3 will still be attached to the drape body 18. The tab 36*b*-2 will still have the bottom ply 12, and thus will not be adhered to the patient; however, the tab 36*b*-3 will be adhered to the patient.

The adhesive of the body sections 24, 26, and 28 do not need to be exposed in the order just described. The release liner of the second end section 28 can be removed prior to the release liner of the first end section 26. Further, either the release liner from either the end sections could be removed prior to the middle section 24.

At this point, the top ply can be removed. As noted, the bottom ply (release liner) remains with the carrier lift tab 36*b*-2, and the top ply of the tab 36*b*-2 remains connected to the top ply of the body. Thus, the top ply can be removed from the middle ply when the drape is adhered to the patient by pulling the tab 36*b*-2 away from the patient. The top ply of the body 18 is monolithic (i.e., continuous), and thus pulling of the tab 36*b*-2 will remove the top ply from the entire drape body 18.

The adhesive adhering the drape to the patient is not a strong adhesive, and we have found that simply pulling on the tab 36*b*-2 can cause the middle ply (which is adhered to the patient) to be lifted off the patient. Utilization of the "press down" tab 36*b*-3 will prevent this. The tab 36*b*-3, as noted above, is adhered to the patient, and is separated from the tab 36*b*-2 by the full cut 48. Thus, personnel can press down on the tab 36*b*-3 while the tab 36*b*-2 is lifted away from the patient. This will hold the middle ply in place against the patient when the personnel begin separating the top ply from the middle ply. For this reason, the press-down tab 36*b*-3 is preferably positioned adjacent to the carrier lift tab 36*b*-2. The tab 36*b*-3 does not need to be held against the patient the whole time the top ply is being separated from the middle ply. Rather, it is enough to start the separation of the top ply from the middle ply, for it is in this initial separation stage that the possibility of the middle ply being pulled off of the patient is the greatest.

The drape, as then applied to the patient, once the tab 36*b*-2 has been pulled, will comprise the drape body 18 and the tab 36*b*-3. The tab 36*b*-3 is separated from the body by a top cut. Thus, the tab 36*b*-3 will still include the top ply, even though the top ply has been removed from the body 18. Thus, the remainder of the drape, at this point, will be only the middle ply 14, which, as noted above, is a highly stretchable, and thus conformable, ply.

With the drape applied to the patient, the medical staff can perform the medical/surgical procedure to the patient. The middle ply is incisable, and thus, an incision can be made directly through the drape. Once the procedure has been completed, the drape (which at this point comprises the middle ply) can remain on the patient. The middle ply can remain in place on the patient during an initial healing stage after the procedure is completed. After a desired period of time, this remaining middle ply can be removed from the patient.

If desired, the top ply can remain on the patient during the procedure. However, the top ply is not very stretchable, and thus may not be comfortable for the patient, long term (i.e., several days to several weeks). Thus, if the top ply remains in place during the procedure, it can be removed from the middle ply (which is a stretchable ply) after completion of the procedure, as described above.

Figure 2:
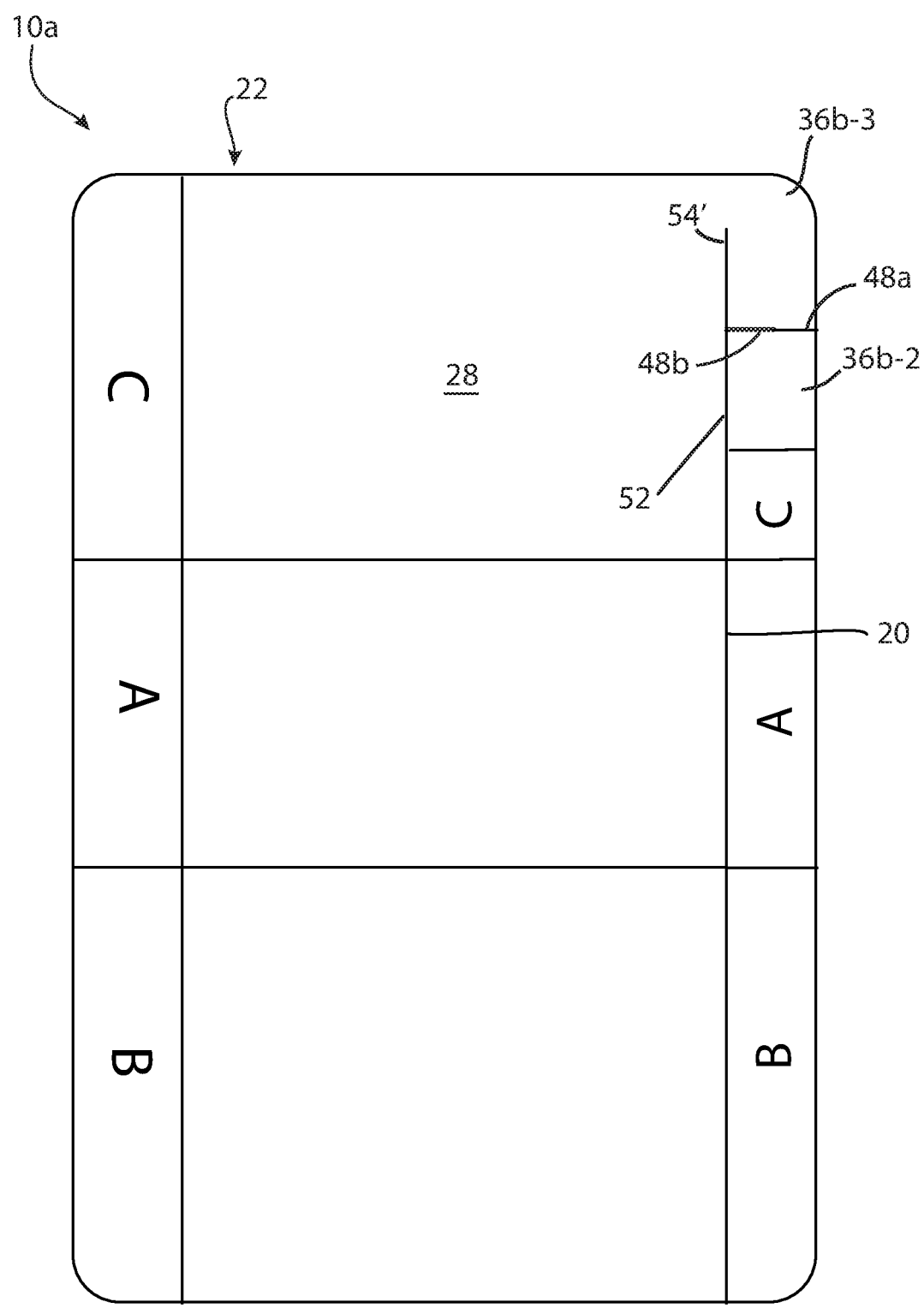
FIG. 2 is a plan view of a variation of the drape of FIG. 1.

As noted, in the drape 10, the top ply remains with the tab 36*b*-3 after the top ply is separated from the middle ply at the end of the medical/surgical procedure. This small section of the top ply can be inadvertently separated from the middle ply, and can, for example, adhere itself to the glove of medical personnel or to an instrument. It would thus be desirable to have this remaining piece of the top ply removed. One way to accomplish this is to provide a finishing step which weeds or removes the top ply from the tab 36*b*-3 during the manufacturing of the drape. However, such alterations to the converting machinery add cost and complexity to the converting machinery. FIG. 2 shows a drape 10*a* which accomplishes the same result without the need for weeding the top ply from the press down tab 36*b*-3. The drape 10*a* of FIG. 2 is virtually identical to the drape 10 of FIG. 1. However, the top cut 54' separating the tab 36*b*-3 from the body upper section 28 does not extend the full length of the tab, as does the top cut 54. Thus, the top cut 54' extends only part of the way to the end edge 22 from the end of the bottom-middle cut 52. Additionally, the cut separating the tab 36*b*-2 from the tab 36*b*-3 is not a complete full cut, as in the drape 10. Rather, the tabs 36*b*-2 and 36*b*-3 are separated by (1) a full cut 48*a* which extends from the side edge 20 of the body about one-half the width of the tabs and (2) a top-middle cut 48*b* which extends from the end of the full cut 48*a* to the junction between the cuts 52 and 54' (i.e. the inner edge of the tabs 36*b*-2 and 36*b*-3). With the top middle cut 48*b* and full cut 48*a* separating the two tabs 36*b*-2 and 36*b*-3, the bottom ply (release liner) of the carrier lift tab 36*b*-2 is connected with the bottom ply (release liner) of the press down section (tab 36*b*-3) such that the release liner under the carrier lift tab will be removed when the C-tab is pulled. Because the top cut 54' does not extend to the edge of the body, when the carrier lift tab is pulled, the top ply will still be removed from the press down tab (36*b*-3).

The cut 48*a*/48*b* is preferably a cut of one type (i.e., either a top-middle cut or a full cut), and the type of cut will depend on the number of plies in the material used for the drape 10*a*. For a 3-ply drape, cut line 48*a* is a full cut, and the release liner on tabs 36*b*-2 and 36*b*-3 remains attached. In the two-ply drape, the cut lines 48*b* is a top middle cut, such that the release liner is removed from both tabs, 36*b*-2 and 36*b*-3 when tab C is operated. Thus, the use of 48*a* and 48*b* in FIG. 2 effectively show two alternatives cut configurations in one drawing.

Application of the drape 10*a* to a patient will be identical to the application of the drape 10. However, at the completion of the procedure, when the top ply 16 is separated from the middle ply 14, the top ply in the tab 36*b*-3 will be removed along with the rest of the top ply. This is due to the fact that the cut 54' does not extend the full length of the tab 36*b*-3, such that the top ply of the tab 36*b*-3 remains connected to the top ply of the body 18, and is therefore indirectly connected to the top ply of the carrier lift tab 36*b*-2.

Figure 3:
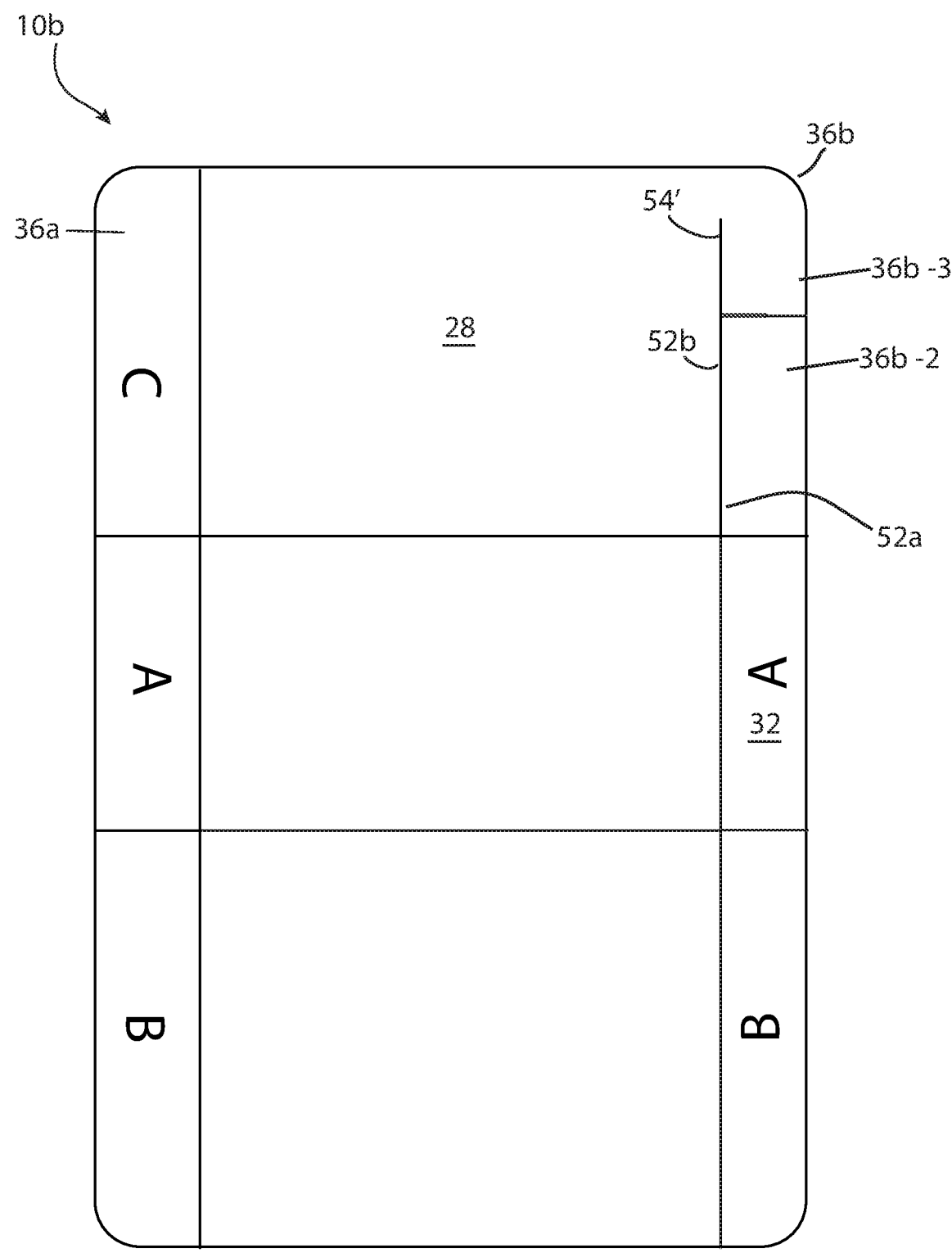
FIG. 3 is a plan view of a variation of the drape of FIG. 2.

FIG. 3 shows a drape 10*b* which is substantially identical to the drape 10*a* (FIG. 2). However, the end tab 36*b* comprises two tabs 36*b*-2 and 36*b*-3, rather than three tabs. The tab 36*b*-3 is identical to the tab 36*b*-3 of the drape 10*a*. The tab 36*b*-2 of the drape 10*b* constitutes a "Carrier Lift Tab" and is separated from the drape body second end section 28 by a bottom cut 52*a* which extends from the edge of the A-tab 32 a short distance, and a bottom-middle cut 52*b* which extends from the end of the bottom cut 52*a* to the opposite end of the tab 36*b*-2, where the cut 54' starts. As can be appreciated, because the tab 36*b*-1 has effectively been eliminated from the tab 36*b*, only tab 36*a* is operable to remove the release liner 12 (bottom ply) from the middle ply 14 in the body second end section 28.

The bottom cut 52*a* may be important if the drape is made from a two-ply material, rather than a three-ply material, as is preferred. In the case of a two ply material, the bottom cut 52*a* will maintain the connection of the substrate ply 14 in the tab with the substrate ply 14 in the body.

Figure 4:
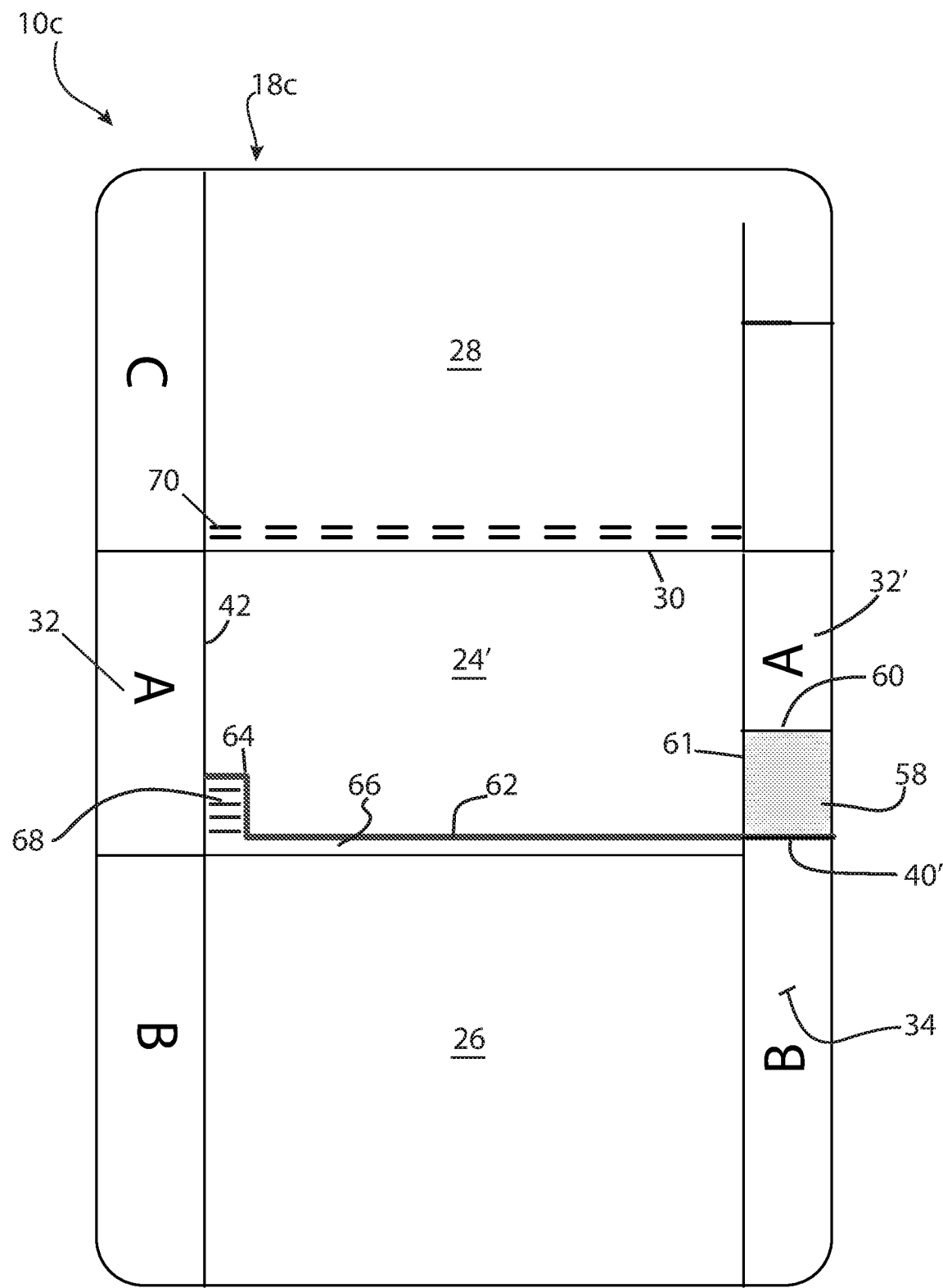
FIG. 4 is a plan view of a variation of the drape of FIG. 3.

The drape 10*c* (FIG. 4) is based on the drape 10*b* (FIG. 3). The drape 10*c* has been modified from the drape 10*b* to allow for the drape to be stretched during application of the drape to a patient. In the drape 10*c,* the A-tab 32' of the middle section 24' is shortened, and the middle section is provided with a liner lift tab 58 positioned between the B-tab 34 and the A-tab 32' which is operable to lift the top ply 16 from the middle ply 14 of the body 18*c*. The liner lift tab 58 is separated from the B and A tabs 34 and 32', respectively, by full cuts 40' and 60, respectively, and is separated from the drape body 18*c* by a bottom-middle cut 61. As seen, the full cut 40' separating the liner lift tab 58 from the B-tab 34 is spaced upwardly (with respect to FIG. 4) relative to the bottom cut 30 which separates the bottom and middle sections 26 and 24', respectively. That is, the full cut 40' is not co-linear with the bottom cut 30. The B-tab 34 is thus slightly longer in the drape 10*c* than in the drapes 10-10*b*. The drape 10*c* further includes a top cut 62 which is co-linear with the cut 40' and which extends from one side edge of the body toward the opposite side of the drape body, but does not extend the full width of the drape body. The top cut 62 is spaced inwardly into the middle section 24' adjacent the bottom cut 30 between the bottom and middle sections 26 and 24', respectively. The drape includes an L-shaped top cut 64 at the end of the top cut 62 and which ends at, or intersects with, the top-middle cut 42 separating the tab 32 from the drape body. In combination, the top cuts 62 and 64 define an L-shaped portion 66 in the top ply 16 extending along the bottom cut 30 between the bottom and middle sections 26 and 24', and which extends along a portion of the top-middle cut 42. The foot of this portion 66 is provided with gauge markings 68. The drape is also provided with a separation stop line 70 adjacent the bottom-cut 30 separating the top and middle sections 28 and 24', respectively. The separation stop line 70 is shown to be in the second end section 28, but could be in the middle section 24'. In use, the operator simply separates the top from the middle ply by lifting the top layer while watching the stop line. When the lift/separation reaches the stop line, the operator stops the lift. There is nothing physically that inhibits the lift. Rather, the stop line 70 is a visual reference point only.

The application of the drape 10*c* to the patient is substantially the same as the drape 10*b*. However, the liner lift tab 58 allows for the top ply in the middle section 24' to be lifted off the middle ply. This breaks the co-adhesive bond between the top and middle plies, and allows the middle section 24' of the drape 10*c* to be stretched (after the bottom ply has been removed) prior to application of the drape middle section to the patient. As noted, the lifting of the top ply from the middle ply breaks the co-adhesive bond between the two plies. Thus, the top ply can be allowed to drop back to rest on the middle ply, without again adhering to the middle ply. Thus, the middle ply can still stretch relative to the top ply. This allows for medical personnel to use the gauge to measure the amount the middle ply of the middle section 24' is stretched by comparing the edge defined by the top cut line 62 with the gauge 68. The middle ply, when stretched, will have a tendency to return to a normal unstretched condition. The greater the extent of the stretch, the greater the "return" force will be. Thus, if desired, the gauge 68 can be provided with indicia indicating the amount of force corresponding to the degree of stretch.

The liner lift tab 58 represents a weedable area. That is, during manufacture of the drape, the bottom and middle plies of the liner lift tab 58 can be removed from the top ply of the liner lift tab. Thus, the drape, as provided, would not have the bottom and middle plies for the liner lift tab 58. If the bottom and middle plies of the liner lift tab were present in the liner lift tab, in the drape as provided, during a procedure, they could be separated from the top ply of the liner lift tab, and could interfere with the procedure. For example, they could adhere to the gloves of medical personnel. By weeding the liner lift tab during manufacture, this concern is avoided.

Figure 5:
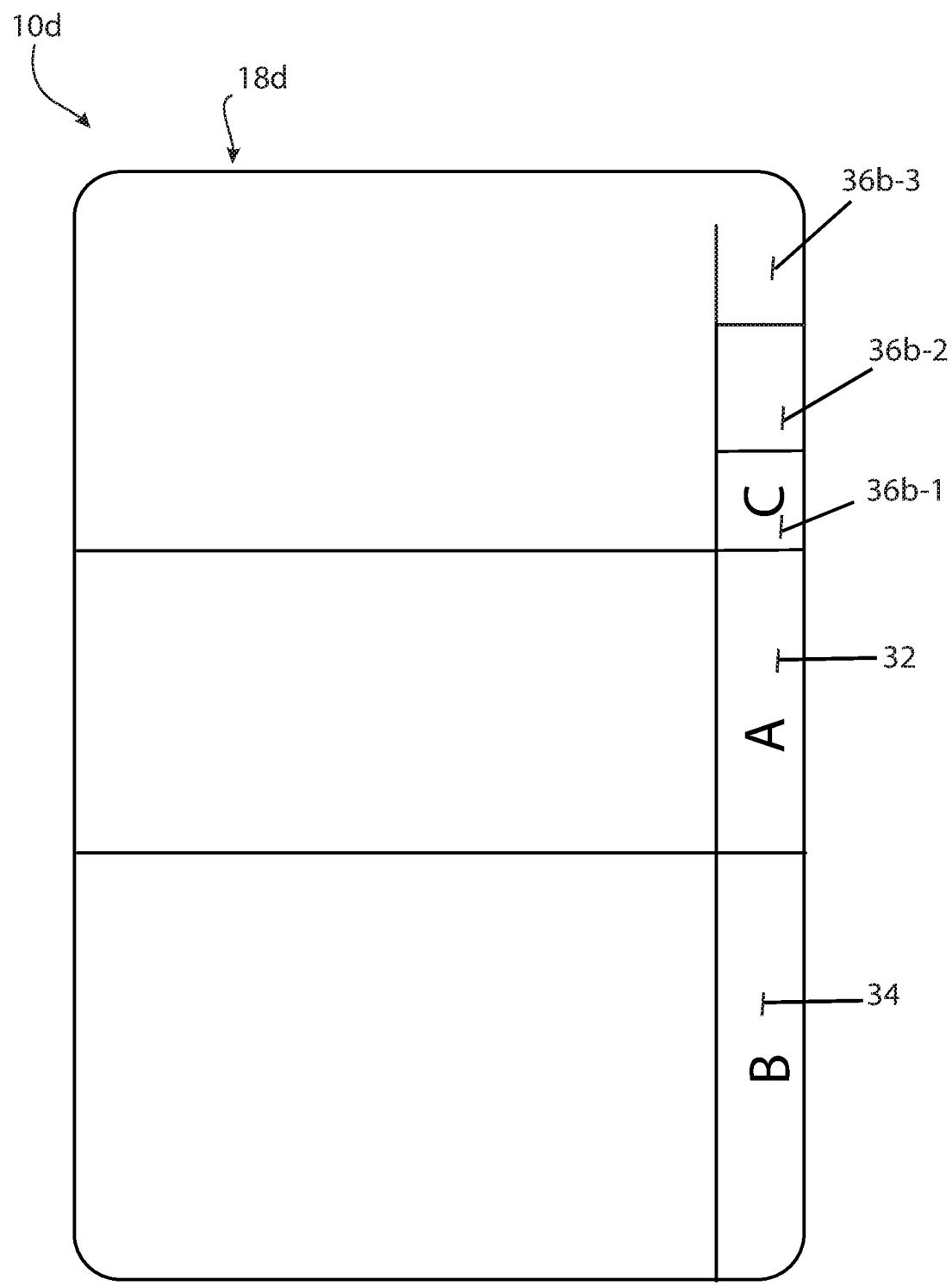
FIG. 5 is a plan view of a second variation of the drape of FIG. 2.

FIG. 5 shows a drape 10*d* which is essentially the same as the drape 10*b* (FIG. 2). However, the drape 10*d* does not have tabs on the left side of the drape (with reference to the figures). Thus, the bottom ply of the drape can only be removed from one side of the drape. Because the drape has tabs along only one side, the drape body 18*d* can be made larger relative to the bodies of the drapes 10-10*c* when the drapes are from the same size tape/film or substrate. The drape 10*d* can thus be used in situations where a larger area of the patient needs to be covered with the drape.

Figure 6:
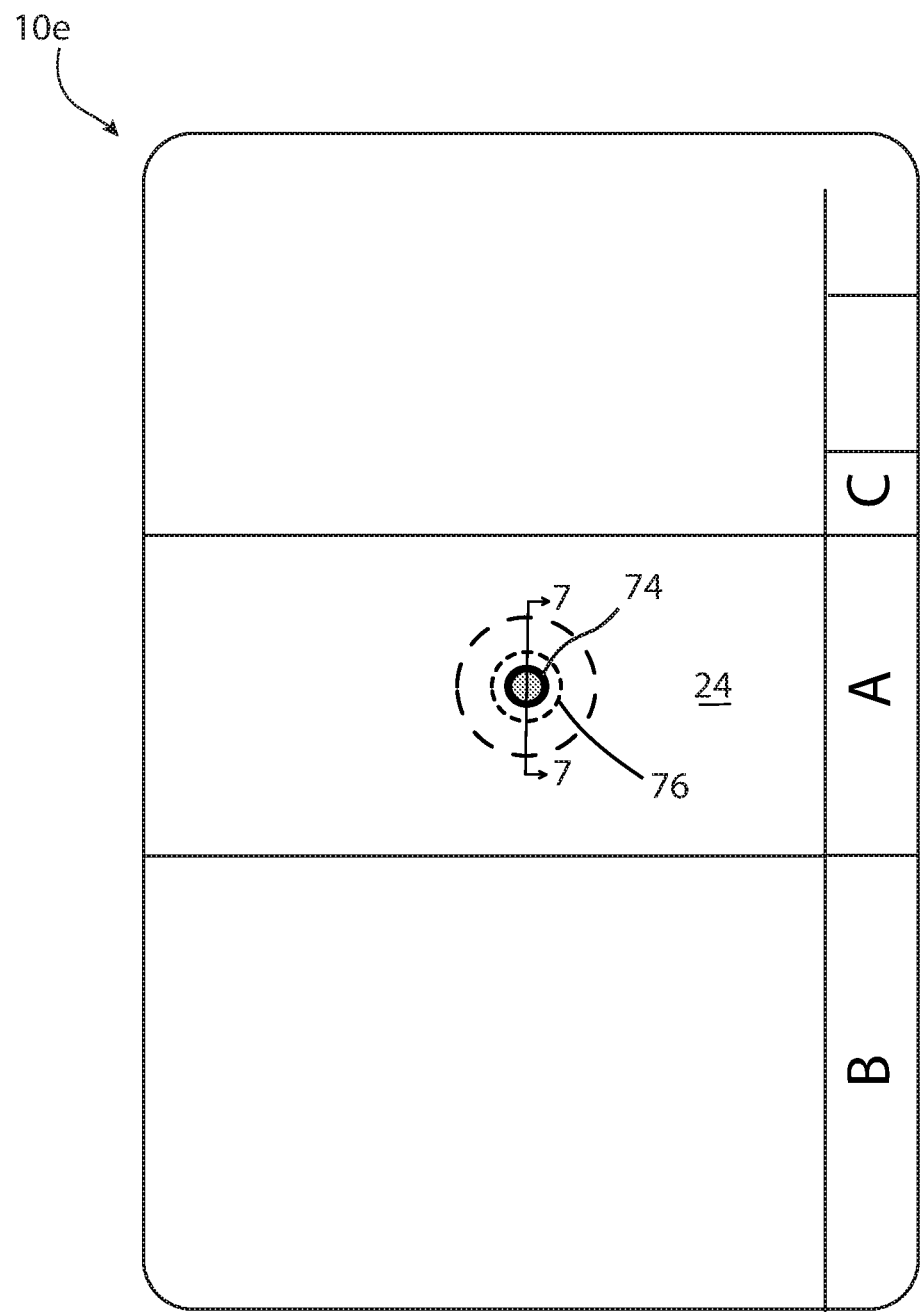
FIG. 6 is a plan view of the drape of FIG. 5, wherein the drape is provided with an access port.
Figure 7:
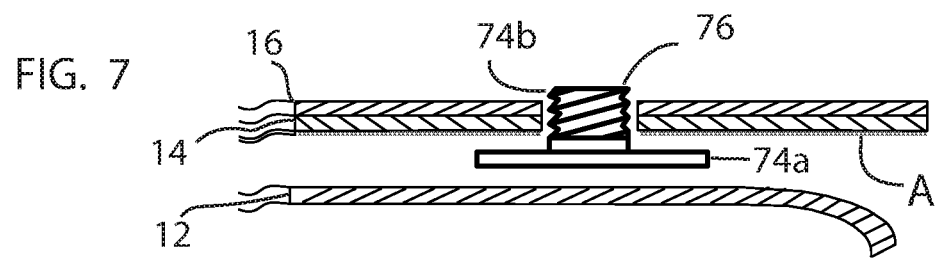
FIG. 7 is a schematic cross-sectional view of the drape of FIG. 6 taken along line 7-7 of FIG. 6.

FIGS. 6 and 7 show a drape 10*e* which is identical to the drape 10*d* of FIG. 5, but which includes with an access port assembly 74 in the middle section 24 to facilitate use of a scope or other instrument with the drape. These ports can be multi-design/multi-function ports and include instrument and scopes.

As seen in FIG. 7, the port assembly 74 comprises a flange 74*a* and a hollow neck 74*b* which extends up from the flange. The neck 74*b* is shown to be externally threaded. The neck 74*b* could, alternatively, be internally threaded, or could be smooth (i.e., without threads). The port assembly 74 can be designed with or without a valve assembly to allow for passage of a scope or instrument through the neck 74*b*. A hole 76 is formed in the middle and top plies 14 and 16, respectively, of the drape and is sized to pass the port assembly neck 74*b* therethrough. The port assembly flange 74*a* is adjacent the underside of the middle ply to be adhered in place by the adhesive of the middle ply. In the as-supplied condition of the drape, the bottom ply 12 will cover the bottom surface of the port assembly base 74a. The drape 10e is preferably made from a two-ply film (which will form the middle and top plies of the drape). The port assembly 74 is then adhered to the two-ply film, and then the release liner (bottom ply) is adhered to the two-ply film as part of a finishing step. Application of the drape 10e to the patient is identical to application of the other drapes to the patient, as described above.

Figure 8A:
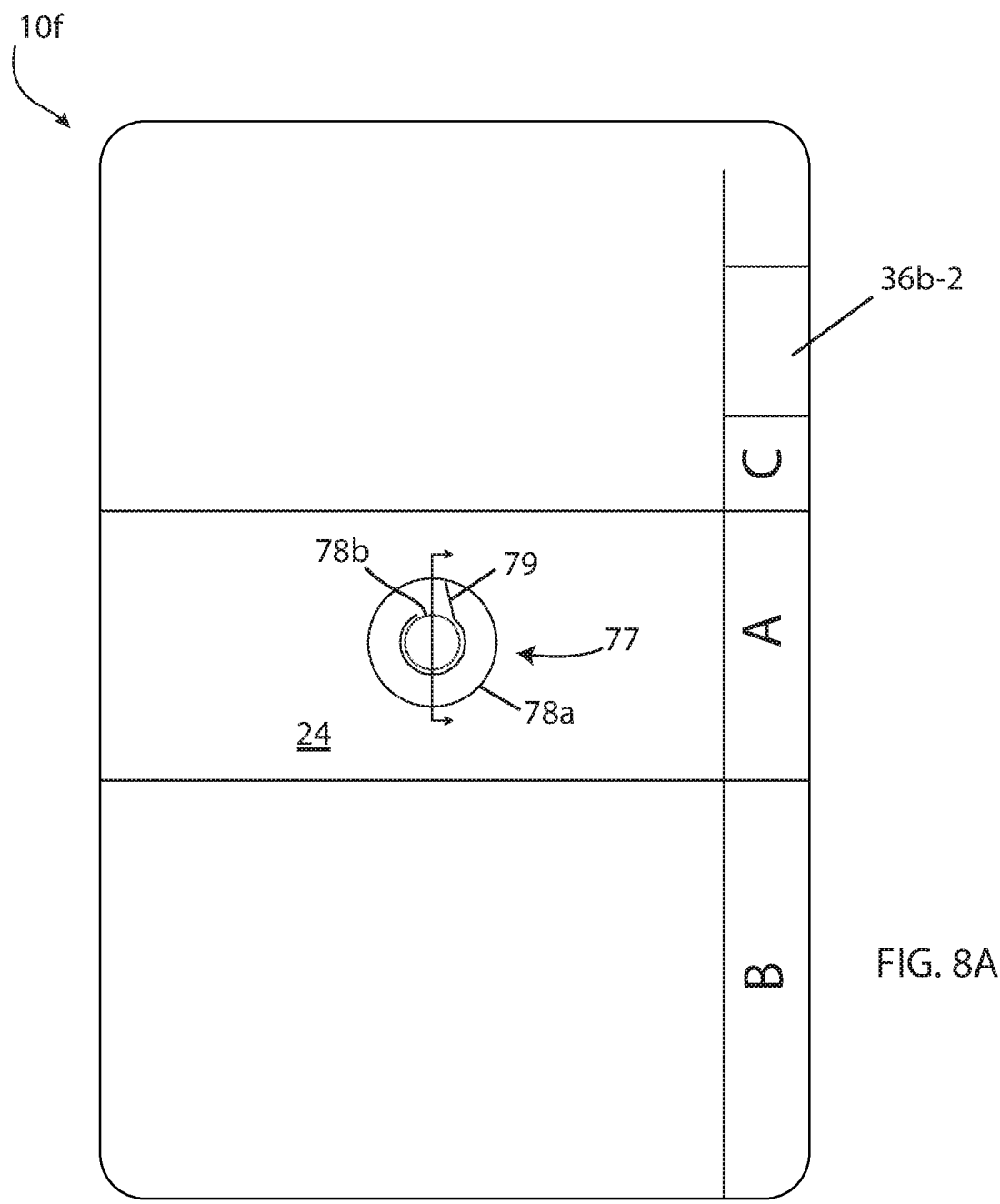
FIGS. 8A and 8B are plan and schematic cross-sectional views of the drape of FIG. 5 provided with the port assembly, but showing different cut lines around the port to allow for optional mounting of the port to the drape.
Figure 8B:
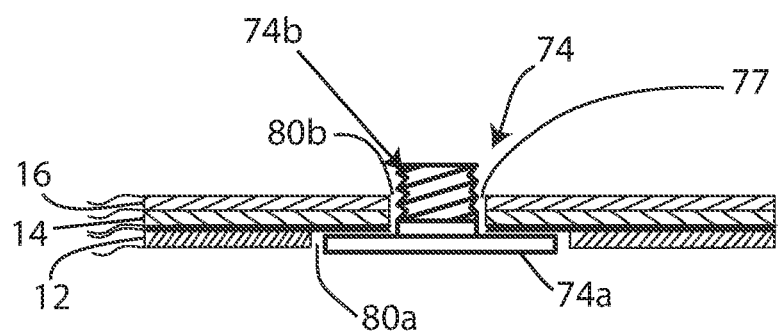

FIGS. 8A and 8B show a drape 10f which is based on the drape 10e (FIG. 6) in which the drape is provided with a port assembly 74. In the drape 10e, the port assembly 74 is pre-assembled with the drape. The drape 10f, on the other hand, is formed to allow the medical personnel to manually adhere the port assembly 74 to the drape. The drape 10f is formed from a 3-ply film which is provided with an openable port assembly aperture 77 defined by an outer bottom cut 78a and an inner top-middle cut 78b that is concentric with the outer bottom cut 78a. The outer bottom cut 78a (FIG. 8A) is sized to form a hole 80a (FIG. 8B) in the bottom ply 12 which will accept the flange 74a (FIG. 8B) of the port assembly 74. The inner, top-middle cut 78b (FIG. 8A) is sized to form a hole 80b (FIG. 8B) in the middle and top plies 14 and 16, respectively, sized to admit the neck 74b (FIG. 8B) of the port assembly 74 to pass therethrough. The top-middle cut 78b (FIG. 8A) defines a "push tab" which when pressed (i.e., pushed downwardly or through the bottom ply), will separate the top and middle plies below the push tab, and the bottom ply, to form the aligned holes 80a,b (FIG. 8B) in the drape prior to removal of the bottom ply from the drape. As can be appreciated, the holes 80a,b in combination define the port aperture 77 (FIG. 8A). Opening the port aperture as just described will expose the adhesive of the middle ply 14 around the opening 80a, and the base/flange 74a of the port assembly can be pressed against the middle ply in the hole 80a to adhere the port assembly 74 in place in the drape 10f. The cuts 78a,b (FIG. 8A) are formed such that, if the port assembly is not going to be used, the respective plies will remain contiguous, that is, the bottom ply surrounded by the cut 78a will be removed when the A-tab is pulled, and the top ply surrounded by the cut 78b will be removed with the carrier lift tab 36b-2 is pulled. The cuts 78a,b could, for example, be perforated cuts, rather than continuous cuts. In addition, the drape includes a scythe-shaped cut 79, comprising a leg which extends from the outer cut 78a towards the inner cut 78b. This leg is not a radially extending cut, but rather defines an acute angle with a diameter of the two port aperture forming cuts 78a,b. An arced cut then extends from the end of this leg, and substantially surrounds the inner cut 78b. The scythe-shaped cut 79 helps with the removal of the material to open the port assembly hole. Other than the optional application of the port assembly 74 to the drape 10f, application of the drape 10f to a patient is identical to application of the prior described drapes.

Figure 9A:
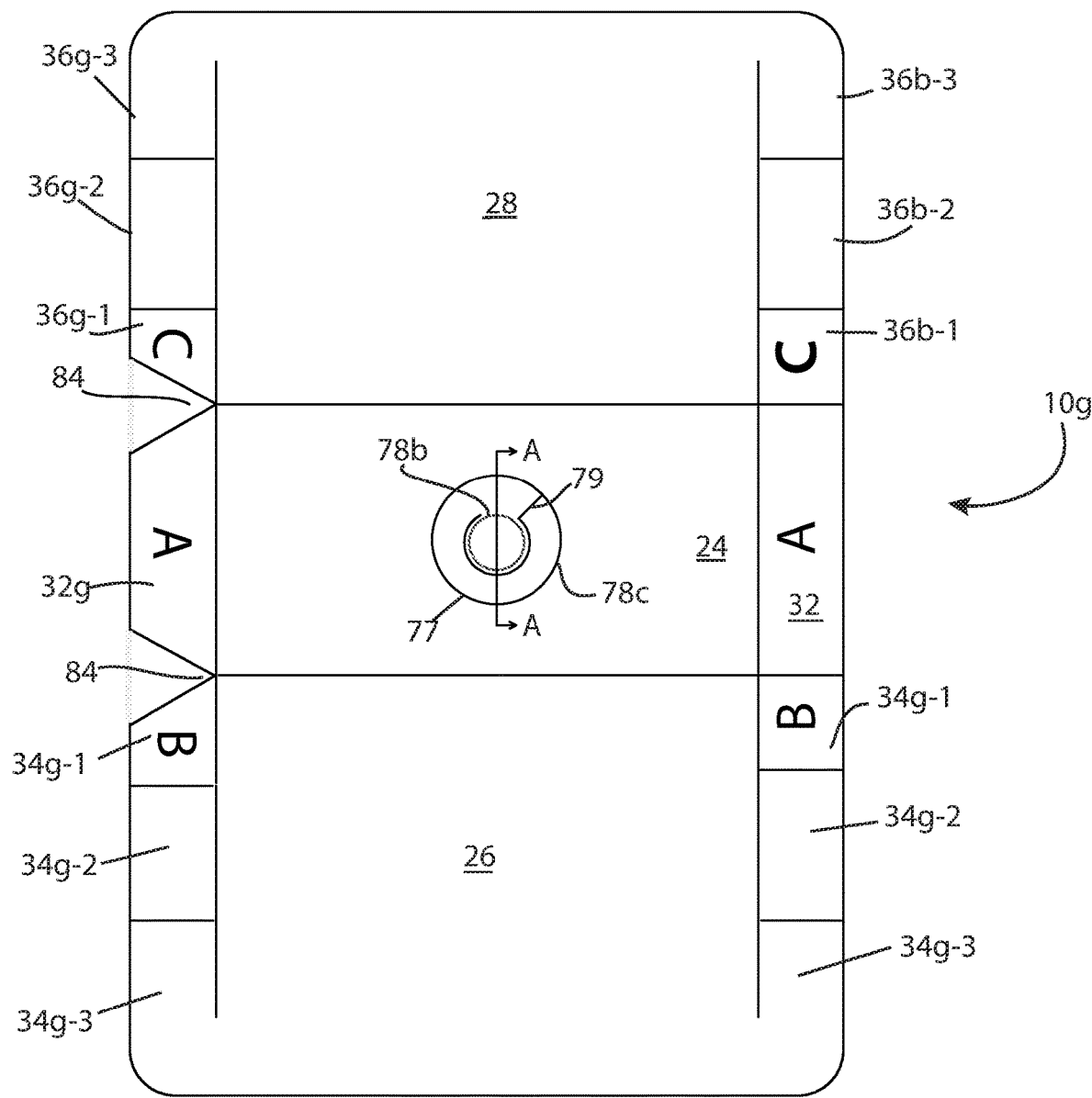
FIG. 9A is a plan view of the drape of FIG. 8, but with tabs along both sides of the drape to allow for dual-sided operation of the drape.
Figure 9B:
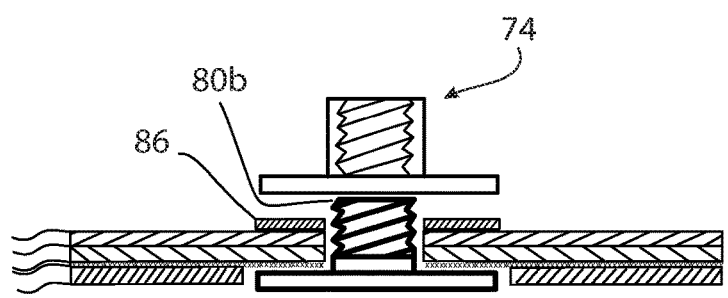
FIG. 9B is a cross-section taken along line A-A of FIG. 9A.

The drape 10g of FIG. 9A is based on the drape 10b (FIG. 2). Like the drape 10f, the drape 10g is provided with port assembly aperture 77 defined by inner and outer cuts 78a,b in the middle section 24. The A-tab 32, the release liner tab 36b-1, the carrier lift tab 36b-2 and the press-down section 36b-3 are unchanged from the corresponding tabs in the drape 10b. The drape 10g, however, is provided with release liner tabs 34g-1 and 36g-1, carrier lift tabs 34g-2 and 36g-2, and press down sections or tabs 34g-3 and 36g-3 on the left side (relative to FIG. 9) of the second end section 28, and on both sides of the first end section 26. Thus, the operability provided by the drape 10b (FIG. 3) is available from both sides of the drape, and from either end section of the drape. In addition, notches 84 are formed between the left side A-tab 32g and the release liner tabs 34g-1 and 36g-1. Additionally, an anti-friction washer 86 is provided around the port assembly aperture hole 80b to reduce abrasions. Lastly, the drape is shown, in FIG. 9B, with both an internally and an externally threaded port assembly. The internally threaded port assembly can be used in lieu of the externally threaded port assembly. Alternatively, the internally and externally threaded ports can be used together. In this instance, one port is threaded into (or onto) the other, such that the drape material is sandwiched between the flanges of the two port assemblies. The port assembly can be fixed to the drape by any desired suitable connection method, i.e., twist lock, friction, quick connect, etc. Alternatively, the flange of the port assembly could be heat sealed to the substrate.

Figure 10A:
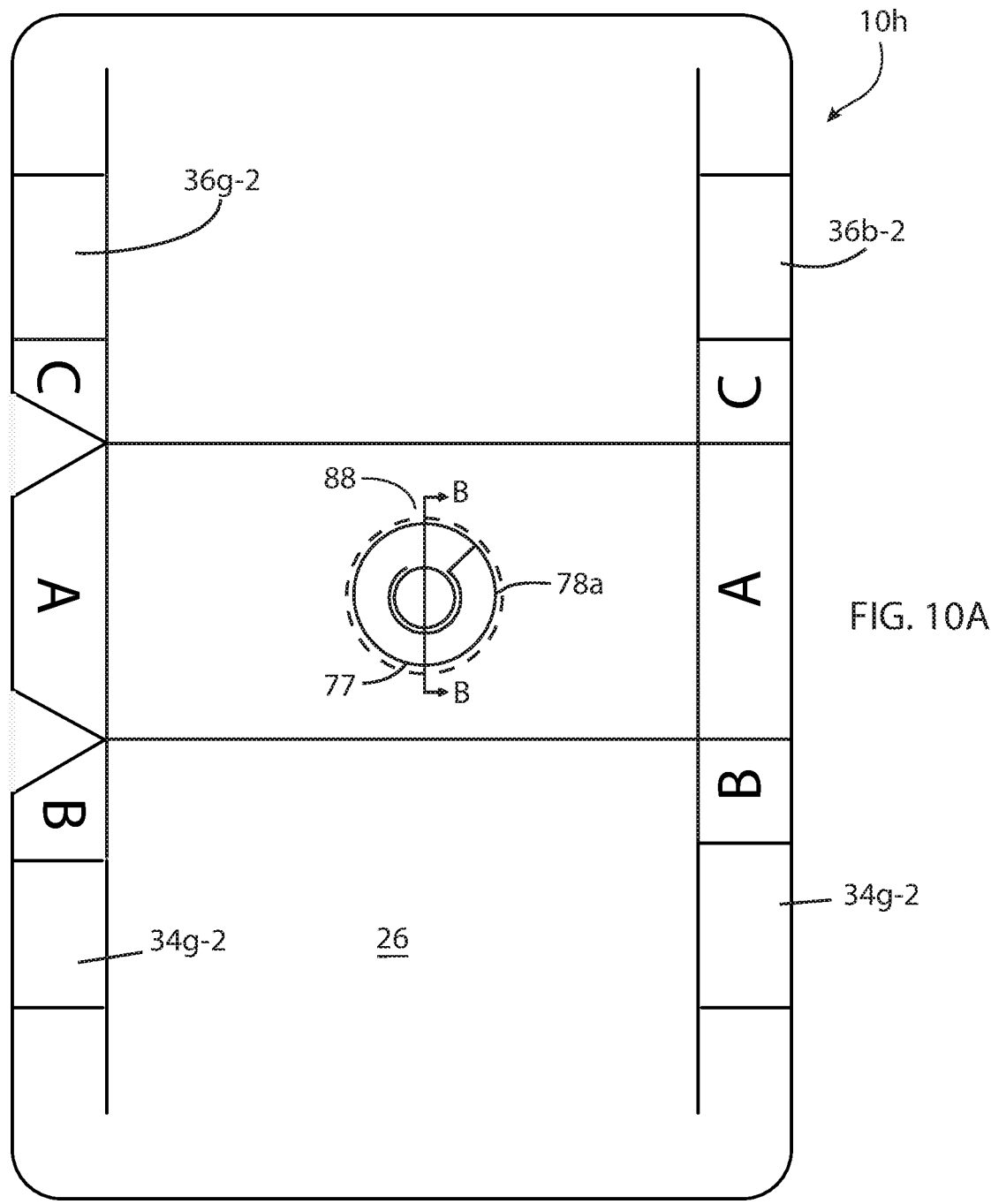
FIG. 10A is a plan view of a variation of the drape of FIG. 9.
Figure 10B:
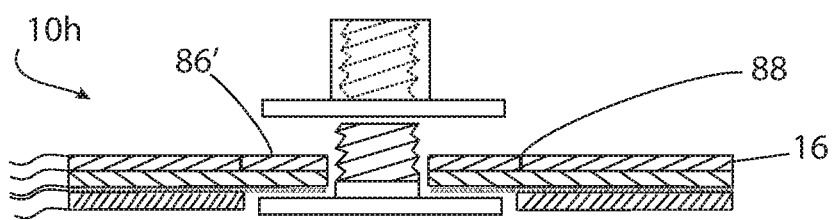
FIG. 10B is a cross-section taken along line B-B of FIG. 10A.

The drape 10h (FIG. 10) is substantially similar to the drape 10g (FIG. 9). However, the drape 10h is provided with a perforated cut 88 in the top ply around the port assembly aperture 77 which is approximately equal in diameter to the bottom cut 78a of the port assembly aperture. In the drape 10h, when the top ply 16 is removed using any of the carrier liner removal tabs 36b-2, 36g-2, or 34g-2, the top ply within the top perforated cut 88 can remain with the middle ply to define the anti-friction washer 86'. Thus, the drape 10h provides for the anti-friction washer without the need for an additional manufacturing step.

Figure 11:
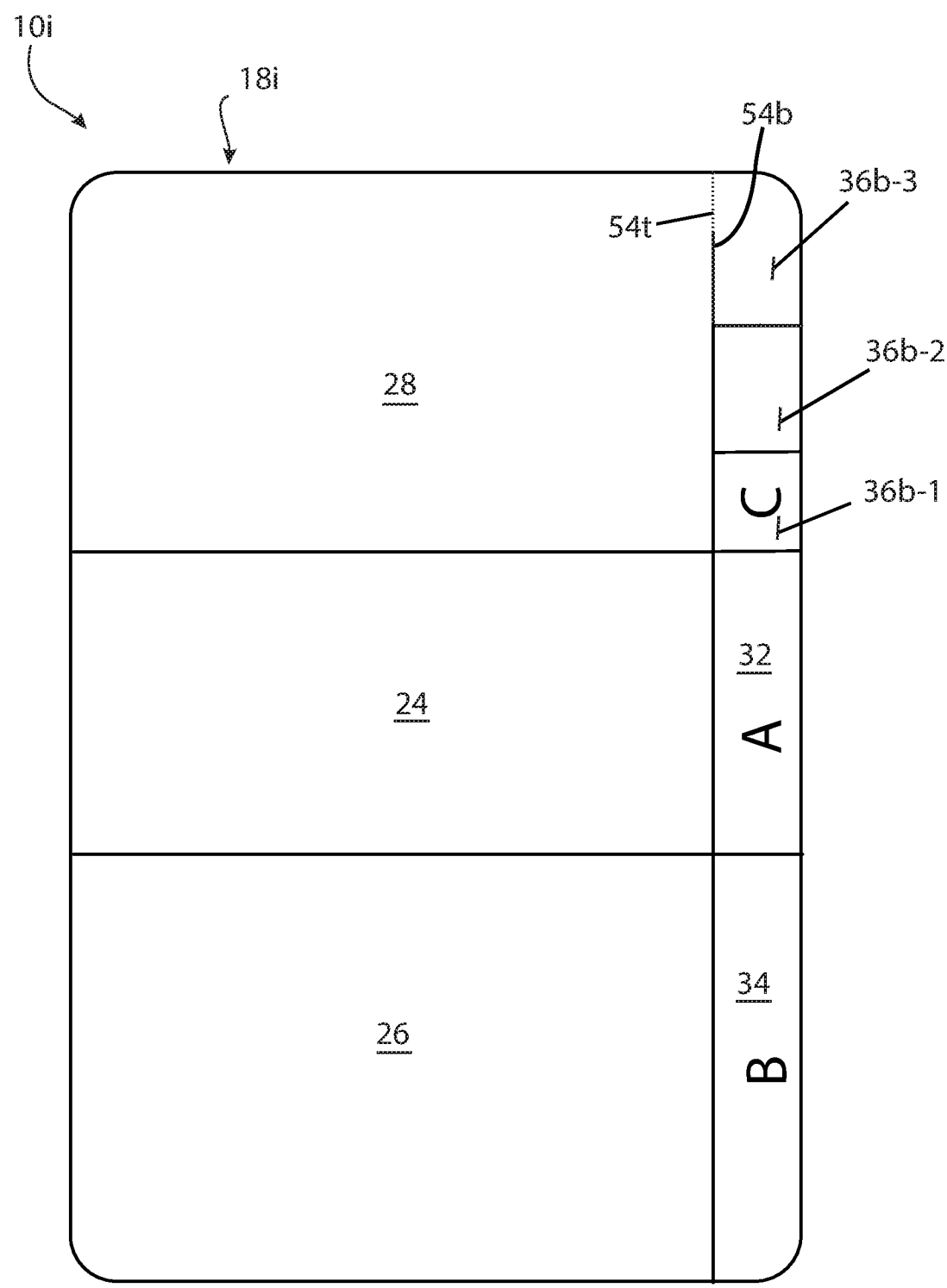
FIG. 11 is a plan view of a drape similar to that of FIG. 1, but wherein the top ply and the bottom ply remain with a "press down" area when the top and bottom plies are removed from the middle ply.

The drape 10i (FIG. 11) is substantially similar to the drape 10 (FIG. 1). However, it has tabs extending along only one edge of the drape body, similarly to the drape 10d of FIG. 5. The drape 10i of FIG. 11 varies from the drape 10 (FIG. 1) in that the tab 36b-3 is separated from the body 18i by a top cut 54t and a bottom cut 54b which extend the length of the tab 36b-3. Thus, only the middle ply of the tab 36b-3 is contiguous or connected to the body 18i. Therefore, the bottom ply and the top ply of the tab 36b-3 will remain with the tab when the release ply tab 36b-1 and the carrier lift tab 36b-2, respectively, are used.

The drape 10j (FIG. 12) shows a further variation of the drape. The drape 10j comprises a body 18j having side edges 20j and top and bottom edges 22j. Unlike the drapes 10-10i, the drape 10j has two section 24j and 26j divided by a bottom cut 30j which extends the width of the body 18j. The two sections 24j, 26j, do not extend to the top and bottom edges of the body. Rather bottom cuts 31j spaced inwardly from the top and bottom edges 22j define the top and bottom edges of the sections 24j and 26j, respectively, to define grasping panels 33j.

As with the drapes 10-10i, the drape 10j has tabs 32j, 34j and 36j extending along each side of the drape. As seen in FIG. 12, the tabs are labeled as "1", "2", and "3", respectively. The tabs are arranged on each side such that each edge of the drape has two tabs 32j between a tab 34j on one end and a tab 36j on the other. Also, as seen, the tabs on one side of the drape are in reverse order relative to the tabs on the other side of the drape, such that there is a tab 36j and a tab 34j at each end of the drape, but on opposite sides of the drape.

A tab 32j extends along each side edge 20j from the cut line 30j, such that each section 24j, 26j has associated tabs 32j. The tabs 32j are separated from the body 18 by a top-middle cut 42j, such that, when the tabs 32j are pulled, the tabs will remove the bottom ply from the drape to expose the adhesive of the middle ply of the sections 24j, 26j for application of the drape to a patient. If desired, each side could be provided with a single elongate tab 32*j*. In such an instance, the cut line 30*j* would not be needed, and the complete backing (bottom) ply would be removed as one piece.

There is a tab 34*j* associated with each of the grasping panels 33*j*. As seen, the tab 34*j* associated with the top grasping panel is shown to be on the right side of FIG. 12, and the tab associated with the bottom grasping area is shown to be on the left side of FIG. 12. The tabs 34*j* extend from the end of their adjacent tabs 32*j* to the respective top or bottom of the drape. The tabs 34*j* are also separated from the body by a top-middle cut 44*j*, such that, when the tabs 34*j* are pulled, the tabs will remove the bottom ply from the drape to expose the adhesive of the middle ply of the grasping areas 33*j*.

The tabs 36*j*, as seen, overlap the grasping areas 33*j*. Thus, the tabs 36*j* extend from an end of the drape past the cut line 31*j*. The tabs 36*j* are separated from the drape body by a full cut 52*j*-1 and a bottom middle cut 52*j*-2. The full cut 52*j*-1 extends from the edge of the drape to the cut line 31*j* to fully separates the tabs 36*j* from the grasping areas 33*j*. The bottom middle cuts 52*j*-2 extend from the cut 32*j* to the end of the tab 36*j* adjacent the tab 32*j*. This bottom middle cut separates the bottom and middle plies of the tabs 36*j* from the bottom and middle plies of the body 18*j*, while leaving the top ply of the tab connected to (or contiguous with) the top ply of the body. As can be appreciated, pulling the tabs 36*j* will remove the top ply of the drape body from the middle ply. To facilitate removal of the top ply from the middle ply, the drape additionally includes a top ply cut 53*j* extending inboardly from the corner junction of each tab 36*j* with the drape body 18*j*. FIG. 12 shows two cuts 53*j*. However, if desired, the drape could be provided with a single cut which extends generally diagonally from one corner to the other. As seen, the cuts 53*j* do not bisect the corner (i.e, do not form angles of 45° with the side or end edges of the drape). Rather, the cut lines 53*j* curve upwardly and inwardly from the edge of the grasping area, and then extend inwardly at an angle of about 30°-40°. At a point approximately one-third of the way across the end of the body 18*j*, the cut 53*j* angles toward the opposite end. Thus, the cut 53*j* has a stylized S appearance.

The drape 10*j* is applied to a patient generally similarly to the drape 10. Initially, the backing or bottom ply of one of the sections 24*j*, 26*j* is removed by pulling a tab 32*j* away from (downwardly relative to) the drape body 18*i*. This will expose the adhesive of the middle ply in the selected section 24*j*, 26*j*, allowing the drape section to be applied (adhered) to the patient. The tab 32*j* for the other of the two sections can then be used to remove the backing from the remaining section to expose the adhesive for that section. As can be appreciated, when the backing is removed from the drape body using the tags 32*j*, the backing remains with the grasping areas 33*j*. Thus, the grasping areas will provide an adhesive free zone which can be gripped by the user. Additionally, removal of the backing using the tabs 32*j* separate both tabs 32*j* for a section from the body. Thus, once the backing has been removed from the drape, and the drape has been applied to the patient, the grasping areas 33*j* will still have the bottom ply, and the tabs 34*j* and 36*j* will remain with the body 18*j*, and will also still have their respective release liners (bottom plies).

Once the drape has been applied to the patient, the grasping areas 33*j* can be folded upwardly, and the release liner (bottom ply) of the grasping areas can be removed using the tabs 34*j*. The middle ply of the grasping areas can then be adhered to the patient. At this point of application, the drape is comprised of the middle and top plies in the body 18*j* and the tabs 36*j* (which still have all three plies). The top ply, as noted above, can be removed from the middle ply at any desired time. As can be appreciated, the top ply extends from end-to-end of the body 18*j*, and at this point in application, is still in place in the grasping areas 33*j*. As noted above, the tabs 36*j* are separated from the grasping areas by the full cuts 52*j*-1. Further, and as also noted above, unless the user presses down on the drape as the top ply is removed from the middle ply, the middle ply may be removed from the patient with the top ply. The cuts 53*j* help prevent this from occurring. When the top ply is removed, the user can press down against the grasping area 33*j* proximate the tab 36*j*, for example, in the oval 55*j*, and then the user can pull up on the tab 36*j*. As the user pulls up on the tab 36*j*, the top ply will separate or split along the cut line 53*j*, and the top ply that is directly connected to the tab 36*j* will separate from the middle ply, while the top ply that is connected to the grasping area will remain in place. Once the separation of the top ply from the middle ply reaches the end of the cut line 53*j*, the possibility that the middle ply will be removed from the patient has been substantially eliminated. The user can thus stop pressing against the drape, and, as the tab 36*j* is continued to be pulled away from the drape, the remainder of the top ply will be removed from the middle ply. If the cut 53*j* extends from one corner to the opposite corner, then the top ply would need to be removed in two parts. Once the top ply has been removed, only the middle ply of the body 18*j* will remain on the patient. The tabs will be fully separated from the body.

The drape 10*j* can optionally be provided with a wound covering sheet 90 which is adhered to the middle ply 14 by means of the middle ply adhesive. Importantly, the sheet 90 has a lower surface 90*a* which is free of adhesive. Thus, the wound covering sheet 90 can be positioned on the drape such that when the drape is applied to a patient, the wound covering sheet 90 will cover the patient's wound. Hence, none of the adhesive of the middle ply will contact the wound. A drape provided with the wound covering sheet 90 will thus present a non-adhesive (or adhesive-free) surface to the wound. The wound covering sheet 90 can have any desired size, as long as its perimeter is smaller than the perimeter of the drape body. Additionally, the drape can be provided with the sheet 90 prepositioned on the drape. Alternatively, the wound covering sheet 90 can be applied to the drape middle ply during application of the drape to a patient. In this instance, the drape 10*j* and wound covering member 90 could be provided together as a kit. Providing the wound covering sheet 90 separately from drape would allow for precise placement of the wound covering sheet 90 by the user. Although the wound covering sheet 90 is shown as with the drape 10*j*, the wound covering sheet 90 can be used with any of the drapes disclosed herein.

The wound covering sheet 90 could, for example, be made from a polymer or any other material which will not adhere to a wound (or to which the wound will not adhere) as the wound heals. That is, there will be no tissue ingrowth. The wound covering sheet 90 preferably will allow liquids, moisture, and gasses to pass through the member. This will allow the drape 10*j*, when provided with the wound covering sheet 90, to be used for negative pressure wound therapy (NPWT). For negative wound pressure treatment, a vacuum port 92 is formed in the drape material above the sheet 90. The drape can then be provided with a connector to place the vacuum port 92, and hence the wound covering sheet and ultimately the wound in communication with a vacuum source. This connector can be any type of connector, so that the port 92 can be connected to the vacuum source, in any desired manner. A preferred material for the wound covering sheet 90 is a hydrophobic material, such as provided by Integrated Healing Technologies of Franklin, Tenn., USA under the name Cutimed® Sorbact®. Cutimed® Sorbact® is a dressing mesh dressing fabric coated with a highly hydrophobic fatty acid derivative (such as dialkylcarbamoyl chloride) that attracts pathogens and binds them. Additionally, the port 92 can be connected to a source of positive pressure, which can then be used to remove the drape, as disclosed, for example, in WO2016160997, which is incorporated herein by reference.

In a variation, the wound covering sheet 90 can be a multi-layered member. In this case, one layer can act as a filter, a second layer can provide medicament, another layer can contain sensors (which can monitor biometric parameters such as temperature, gas concentrations, presence of pathogens, etc.). The wound covering sheet can also include, or be made from, a material which when cut defines a plurality of fingers radiating from a central point can act as a check valve. When negative pressure (i.e., a vacuum) is applied to the drape, the fingers of the material will material open up (towards the vacuum source) and allow for the flow of gasses and liquids. When positive pressure is applied, the fingers will lay down flat thereby closing off the openings, restricting flow of liquids, gases, etc. through the member towards the wound. The sheet 90 can be made from any combination of these materials, which can then define separate layers of the sheet 90. As can be appreciated, the layer that will contact the wound will present an adhesive-free surface to the wound and will be made from a material which will substantially prevent ingrowth.

Figure 13:
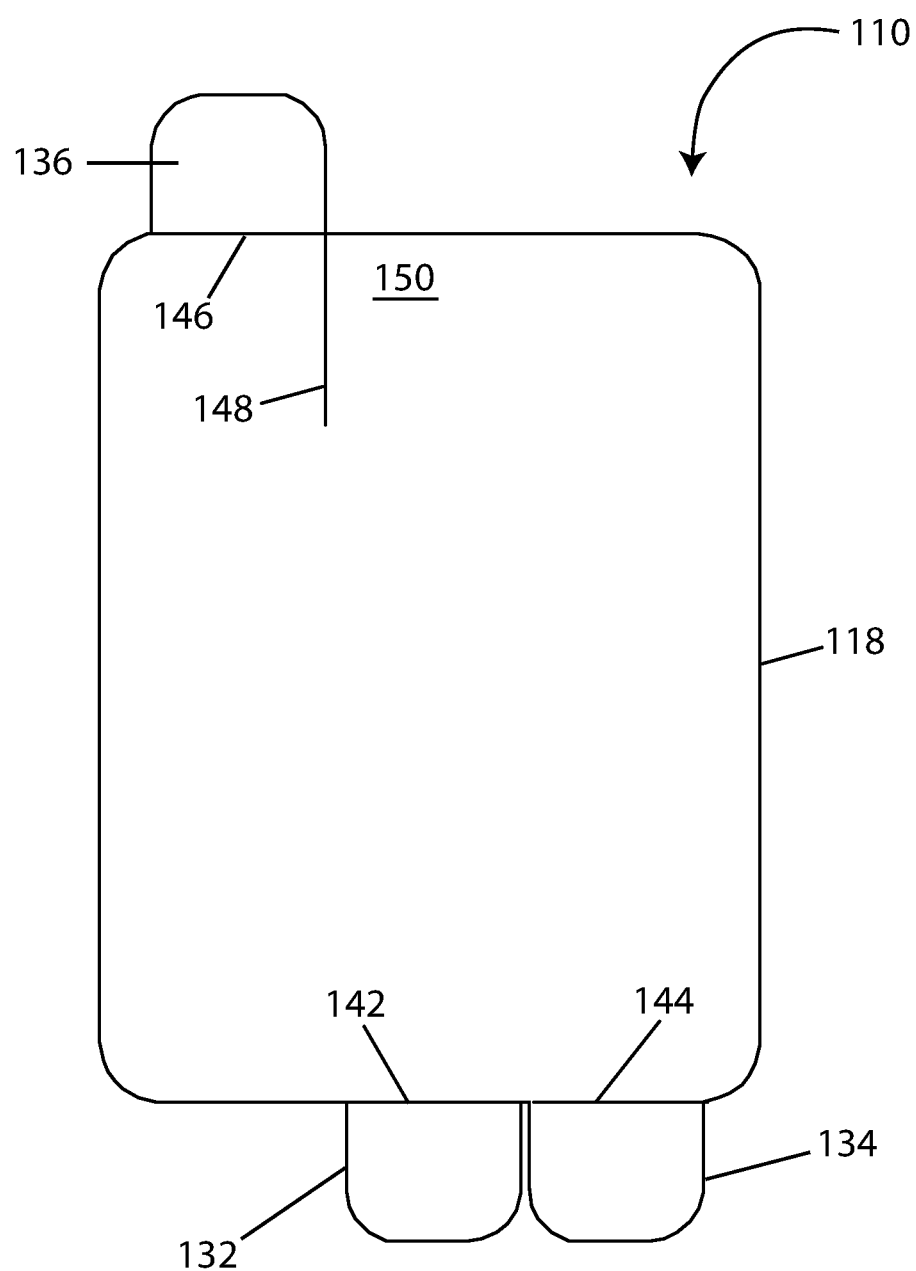
FIG. 13 is a plan view of a second embodiment of the drape.
Figure 14:
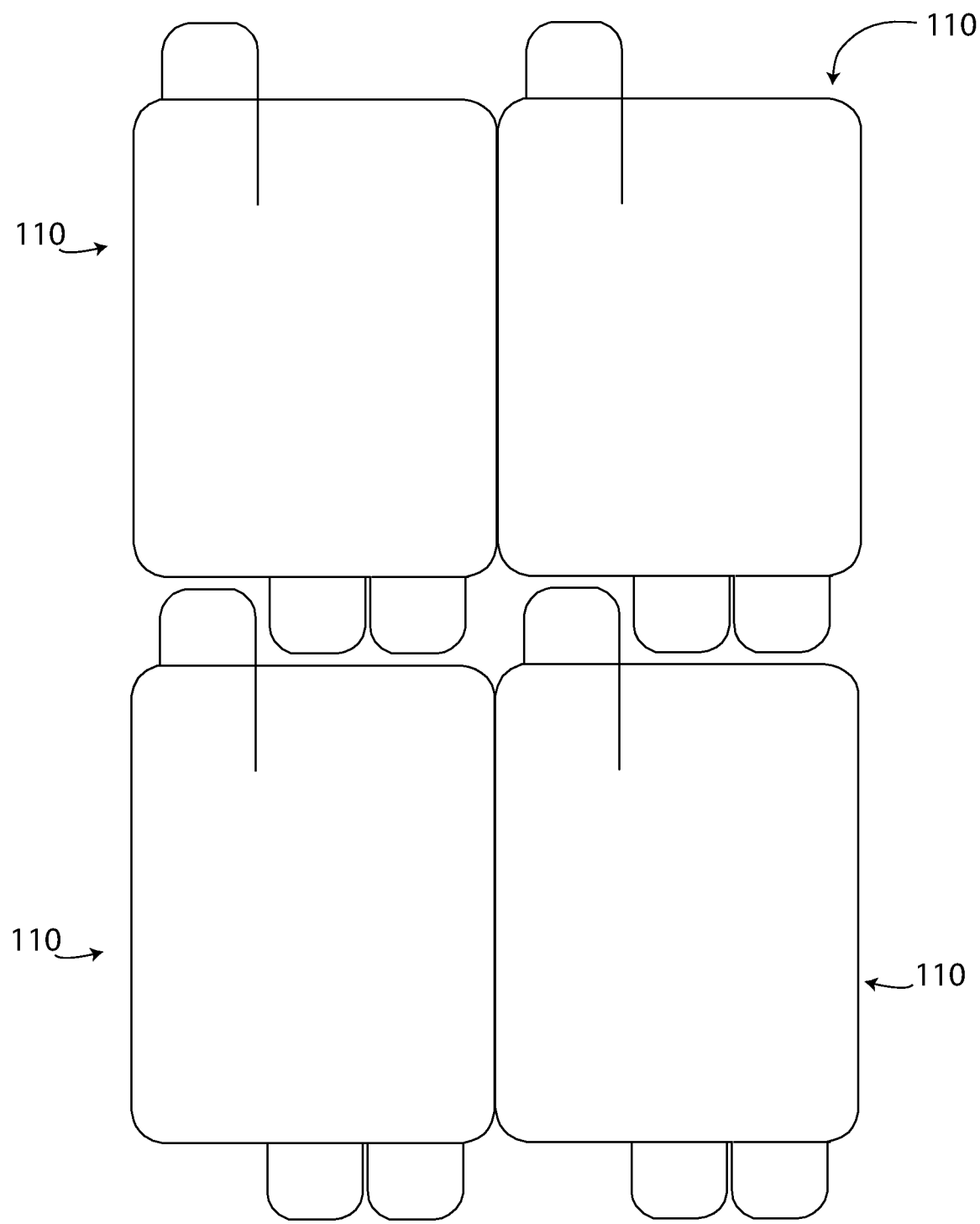
FIG. 14 is a plan view showing the layout for cutting multiple drapes of FIG. 13 simultaneously.

A second embodiment of the drape is shown in FIG. 13. The drape 110 of FIG. 13 is intended to be smaller than the drapes 10-10*h*. Further, as seen in FIG. 14, the shape of the drape 110 allows for drapes to be "nested" in the die-cutting process, to reduce the amount of waste produced during manufacture of the drape.

Returning to FIG. 13, the drape 110, like the drapes 10-10*j*, is formed from a three-ply material. The drape 110 includes a body 118 with three tabs, 132, 134, and 136 extending from the body. As seen, the tabs 132 and 134 extend from one edge of the body, and the tab 136 extends from the opposite edge of the body. Further, the tabs 132 and 134 are adjacent each other, and are proximate, for example, the right side of the bottom edge of the body; and the tab 136 is proximate the left side of the top edge of the body (all with respect to FIG. 13). This alternating positioning of the tabs allows for nested production of the drapes as noted above and shown in FIG. 14. The tab 132 is separated from the drape body by a top-middle cut 142; the tab 134 is separated from the drape body by a bottom cut 144; and the tab 136 is separated from the body by a bottom-middle cut 146. Thus, the bottom ply of the tab 132 is connected with the bottom ply of the drape body; the top and middle plies of the tab 144 are connected to the top and middle plies of the body; and the top ply of the tab 136 is connected to the top ply of the body. Lastly, a top cut 148 extends inwardly into the body 118 and is co-linear (or an extension of) an inner edge of the tab 136.

To apply the drape 110 to a patient, personnel hold tabs 132 and 134. The top-middle cut 142 separating the tab 132 from the body 118 enables the bottom layer of the drape body 118 to be removed by pulling the tab 132 away from the drape body. The tab 134 provides for a grab area on to which the user can hold while the tab 132 is deployed, and thus defines a separation handle. When the bottom (release liner) layer has been removed from the body, the bottom layer will remain with the tabs 134 and 136. These thus provide for holding areas in which the adhesive of the middle layer has not been exposed. Thus, the medical personnel can hold the drape by the two tabs to position the drape on the patient and to apply the drape to the patient. After the drape 110 has been applied, the top ply can be removed from the middle ply by pulling the tab 136 upwardly away from the drape body 118 and the patient. As such, the tab 136 is a "carrier lift" tab. The area 150 of the drape body to the right of the tab 136 (with reference to FIG. 10) defines a "press down area" which can be pressed against the patient while the tab 136 is being pulled up. As explained above, this reduces the tendency for the middle ply to be pulled off of the patient when the tab 136 is used. The tab 134 is separated from the body by a bottom middle cut, and thus the top ply of the tab 134 remains connected to the top ply of the body. When the tab 136 is used to remove the top ply from the drape body, the top ply of the tab 134 will be removed as well. As with the drapes 10-10*h*, the top ply can remain with the middle ply during the procedure to be removed at the end of the procedure, or it can be removed at the beginning of the procedure. Additionally, although not shown, the drape 110 can be provided with a port assembly access hole to allow for a port assembly to be added to the drape.

As various changes could be made in the above constructions without departing from the scope of the invention, it is intended that all matter contained in the above description or shown in the accompanying drawings shall be interpreted as illustrative and not in a limiting sense. For example, the body of any of drapes 10-10*h* could be formed with just one or two sections (rather than three sections), or could be formed with four or more sections, as may be desired. The number of sections would affect how much of the adhesive of the middle ply is exposed at any one time. Regardless of the number of sections, each section is provided with at least one tab operable to remove the bottom ply (release liner) from the respective section. In addition, regardless of the number of sections, the drape includes at least one "carrier lift" tab to remove the top ply from the middle ply after application of the drape to a patient. Preferably, the drape, regardless of the number of sections, will also have a "press down" tab adjacent the "carrier lift" tab. The carrier separation tab 58 (FIG. 4) can be provided to any of the drapes to allow for a stretchable area. The size of the stretchable area can be changed by altering the distance between the cut lines 62 and 70. Further, the stretch zone can be placed in any of the sections of the drape. The port assembly 74 can be provided with any of the drape variations/embodiments and can be placed in any of the three sections. The tab 36*b*-2 which is operable to lift the top ply from the middle ply can be associated with any of the sections (including the positioning section) of the drape. The press-down section 36*b*-3 is preferably adjacent the top ply lifting tab 36*b*-2, regardless of the position of the top ply lifting tab. These variations are merely illustrative.

The invention claimed is:

1. A medical drape formed from a multi-ply film, said film comprising at least a bottom ply in the form of a release liner, a middle ply which is adapted to be adhered to a patient during use of the drape, and a top ply covering said middle ply; said middle ply having an adhesive applied to a bottom surface of said middle ply to removably adhere said bottom ply to said middle ply; said drape comprising:

a drape body defining top and bottom edges and first and second side edges;

a first liner release tab at an edge of said body; said first liner release tab having an inner edge defined by a top-middle cut, such that operation of said first liner release tab will pull the bottom ply from said middle ply to expose the adhesive of the middle ply; and a carrier lift tab at an edge of said body, said carrier lift tab having an inner edge defined by a bottom-middle cut, such that operation of said carrier lift tab removes the top ply from said middle ply.

2. The medical drape of claim 1 wherein said drape further comprises a press down area adjacent said carrier lift tab such that a user can press against the press down area when the carrier lift tab is being pulled.

3. The medical drape of claim 2 wherein said press down area is defined by a top cut extending inwardly into said body; said top cut being substantially co-linear with an edge of said carrier lift tab.

4. The medical drape of claim 3 including a separation handle extending from said body adjacent said liner release tab; said separation handle being separated from said drape body by a bottom cut.

5. The medical drape of claim 2 wherein said press down area is defined by a tab extending from said body; said press down tab having an inner edge defined by a top cut.

6. The medical drape of claim 5 wherein the top cut defining the inner edge of the press down tab extends the full length of the press down tab.

7. The medical drape of claim 5 wherein the top cut defining the inner edge of the press down tab extends from an edge of said press down tab adjacent said carrier lift tab only a portion of the length of said press down tab, such that the top ply of said press down tab will be removed when said carrier lift tab is pulled.

8. The medical drape of claim 2 including at least one bottom cut in said bottom ply extending from one side edge to the other of said drape body; said at least one bottom cut dividing drape into a first section and a second section; one of said first and second sections being a positioning section; said first liner release tab being associated with said first section; said carrier release and press down tabs being associated with one of said first and second sections; said drape further including a second liner release tab associated with said second section.

9. The medical drape of claim 1 wherein the top-middle cut and the bottom-middle cut separating said liner release and carrier lift tabs, respectively, from said drape body are formed such that upon application of said drape to a patient, and upon removal of said bottom ply and said top ply from said middle ply, none of the release tab or the carrier lift tab remain with the middle ply.

10. The medical drape of claim 1 including a second liner release tab along an edge of said body opposite said first liner release tab.

11. The medical drape of claim 1 wherein said middle ply has a stretchability factor greater than a stretchability factor of the top ply.

12. The medical drape of claim 11 wherein said middle ply has a stretchability factor of at least 200%.

13. The medical drape of claim 1 wherein said drape further includes a liftable panel defined by a top cut extending from one side of said drape body to the opposite side of said drape body and a perforated top cut extending across said body spaced from said top cut and a carrier lift tab associated with said top ply liftable panel; whereby, said top ply liftable panel can be raised from said middle ply to allow for stretching of the middle ply prior to application of the middle ply to a surface.

14. The medical drape of claim 1 wherein said drape is provided with an access port assembly; said access port assembly comprising a flange which is adhered to the adhesive of said middle ply and a hollow neck which extends through an access port aperture in said middle and top plies of said drape body.

15. The medical drape of claim 14 wherein said access port aperture is pre-formed in said drape body.

16. The medical drape of claim 15 wherein said access port is defined by an outer bottom cut and an inner top-middle cut surrounded by said outer bottom cut, said outer bottom cut defining a hole in said bottom ply sized to receive the flange of said port assembly, and said inner top-middle ply defining a hole extending through said top and middle plies sized to allow passage of said access port neck therethrough, whereby said access port aperture is formed by removing the material inside of said outer bottom cut and inner top-middle cut from said drape.

17. The medical drape of claim 15 wherein said access port aperture is defined by concentric holes in said top and middle ply, and wherein said access port assembly is secured to said drape, as supplied.

18. The medical drape of claim 1 including a grasping panel extending across said body at an end of said body; said grasping panel being separated from the remainder of said body by a bottom middle cut such that the bottom ply of said grasping panel remains with said grasping panel when the bottom ply is removed from the remainder of said body.

19. The medical drape of claim 18 including a second release liner tab associated with said grasping panel; said release liner tab having an inner edge defined by a top-middle cut, such that operation of said second liner release tab will pull the bottom ply from said middle ply of said grasping panel to expose the adhesive of the middle ply of the grasping panel.

20. The medical drape of claim 18 wherein said carrier lift tab extends from an end of said drape adjacent said grasping panel; said carrier lift tab extending beyond an inner edge of said grasping panel; said carrier lift tab being separated from said grasping panel by a full cut; and a remainder of said carrier lift tab being separated from the body by a bottom middle cut.

21. The medical drape of claim 20 including a top cut extending diagonally inwardly from a corner of said grasping panel.

22. The medical drape of claim 1 including a sheet having a non-adhesive surface; said sheet being pre-adhered to or being adherable to, said adhesive of said middle ply, such that said drape presents an adhesive-free area which can be applied against a wound; said sheet being made, at least in part, from a material which will prevent ingrowth of the wound to the material as the wound heals.

23. The medical drape of claim 22 wherein the sheet is made from a material which will permit moisture, vapor, and gas to pass therethrough.

24. The medical drape of claim 23 including an aperture formed, or formable, in said drape material above said sheet; said drape being adapted to connect said aperture to a vacuum source, such that said drape can be used for negative pressure wound therapy.

25. The medical drape of claim 22 wherein said sheet is comprised of two or more plies; said plies of said sheet being selected from two or more of a material which acts as a filter, a material adapted to provide medicament to the wound, a material which contains sensors for monitoring biometric and/or physiological parameters (such as temperature, gas concentrations, presence of pathogens, etc.), and a material which operates as a check valve; wherein the material that will be adjacent the wound presents an adhesive-free surface to the wound.

* * * * *